(12) United States Patent
Casado et al.

(10) Patent No.: US 10,028,857 B2
(45) Date of Patent: Jul. 24, 2018

(54) METHODS AND SYSTEMS FOR OSTOMY CARE

(71) Applicant: ConvaTec Technologies Inc., Las Vegas, NV (US)

(72) Inventors: Terese Casado, Princeton Junction, NJ (US); Victoria Schafer, Lansdale, PA (US); Teresa Slankard, Fenton, MO (US)

(73) Assignee: CONVATEC TECHNOLOGIES INC, Las Vegas, NV (US)

( * ) Notice: Subject to any disclaimer, the term of this patent is extended or adjusted under 35 U.S.C. 154(b) by 72 days.

(21) Appl. No.: 13/840,582

(22) Filed: Mar. 15, 2013

(65) Prior Publication Data
US 2014/0236111 A1    Aug. 21, 2014

Related U.S. Application Data

(60) Provisional application No. 61/765,629, filed on Feb. 15, 2013.

(51) Int. Cl.
| | | |
|---|---|---|
| *A61F 5/445* | (2006.01) | |
| *A61F 5/44* | (2006.01) | |
| *A61F 5/443* | (2006.01) | |
| *A61F 5/448* | (2006.01) | |

(52) U.S. Cl.
CPC ................ *A61F 5/445* (2013.01); *A61F 5/44* (2013.01); *A61F 5/443* (2013.01); *A61F 5/448* (2013.01)

(58) Field of Classification Search
CPC .. A61F 5/445; A61F 5/44; A61F 5/443; A61F 5/448
USPC .......................................................... 604/332
See application file for complete search history.

(56) References Cited

U.S. PATENT DOCUMENTS

| | | | | |
|---|---|---|---|---|
| 6,171,289 B1 * | 1/2001 | Millot | ...................... | A61F 5/443 604/336 |
| 6,304,854 B1 * | 10/2001 | Harris | .................... | G06Q 30/02 705/26.62 |
| 6,342,037 B1 * | 1/2002 | Roe | ......................... | A61F 13/42 422/1 |
| 6,709,421 B1 * | 3/2004 | Falconer | ................. | A61F 5/441 604/335 |

(Continued)

OTHER PUBLICATIONS

Beitz, et. al., "Content Validation of a Standardized Algorithm for Ostomy Care"; Ostomy Wound Care, v.56, pp. 44-53 (2010).*

(Continued)

*Primary Examiner* — Todd J Scherbel
*Assistant Examiner* — Guy K Townsend
(74) *Attorney, Agent, or Firm* — Wilson Sonsini Goodrich & Rosati

(57) ABSTRACT

Disclosed are computer-based systems and media for providing an interactive ostomy treatment guide, and methods of using the same, the guide comprising: a software module configured to receive ostomy assessment information, the assessment information comprising one or more of: condition of skin adjacent an ostomy, topographical location of any peristomal lesion, stoma type, pouching surface type, stoma devices present, and stoma complications; a software module configured to apply a treatment algorithm to the ostomy assessment information to generate an output; and a software module configured to display one or more ostomy management options based on the output.

14 Claims, 63 Drawing Sheets

(56) References Cited

U.S. PATENT DOCUMENTS

| | | | | |
|---|---|---|---|---|
| 7,076,371 B2* | 7/2006 | Fu | ............................ | A61B 5/082 702/19 |
| 7,160,275 B2* | 1/2007 | Falconer | .................. | A61F 5/441 604/333 |
| 7,737,321 B2* | 6/2010 | Elliott | ..................... | A61F 5/445 200/61.04 |
| 7,830,519 B2* | 11/2010 | Mah | .................... | A61B 5/14532 356/434 |
| 7,858,839 B2* | 12/2010 | Elliott | ..................... | A61F 5/445 200/61.04 |
| 8,398,603 B2* | 3/2013 | Thirstrup | ................. | A61F 5/445 602/41 |
| 8,740,865 B2* | 6/2014 | Krystek | ................... | A61F 5/445 340/605 |
| 2003/0008407 A1* | 1/2003 | Fu | ............................ | A61B 5/082 436/161 |
| 2005/0015065 A1* | 1/2005 | Falconer | .................. | A61F 5/441 604/335 |
| 2005/0085923 A1* | 4/2005 | Levine | ............... | A61B 17/0401 623/23.65 |
| 2005/0267595 A1* | 12/2005 | Chen | ....................... | A61F 5/003 623/23.65 |
| 2007/0004958 A1* | 1/2007 | Ohdaira | .................. | A61B 17/02 600/12 |
| 2010/0131075 A1* | 5/2010 | Ludlow | ................... | A61L 27/18 623/23.66 |
| 2010/0191203 A1* | 7/2010 | Haraldsted | .............. | A61F 5/448 604/343 |
| 2013/0261575 A1* | 10/2013 | Kiyoshi | .................. | A61F 5/445 604/339 |
| 2013/0324952 A1* | 12/2013 | Krystek | .................. | A61F 5/445 604/318 |
| 2014/0236111 A1* | 8/2014 | Casado | .................... | A61F 5/445 604/332 |

OTHER PUBLICATIONS

Turnbull, The importance of coordinating ostomy care and teaching across settings. *Ostomy Wound Management*. 2002, 48(5):12-13.

Cross, Staff nurses confidence and barriers in caring for ostomy patients. *Journal of Wound Ostomy and Continence Nursing*. 2012, 39(3) (suppl). Abstract 6002.

Jones et al., Fecal ostomies practical management for the home health clinician. *Home Healthcare Nurse*. 2011, 29(5):306-317.

Boarini et al., Roles of the ostomy nurse specialist: historical perspective, role potential. In: Colwell J, Goldberg MT, Carmel JE., Fecal and Urinary Diversions Management Principles. St. Louis: Mosby; 2004, p. 22.

Beitz et al., Content validation of a standardized algorithm for ostomy care. Ostomy Wound Management. 2010, 56(10):22-38.

Bales I., Testing a computer-based ostomy care training resource for staff nurses. *Ostomy Wound Management*. 2010, 56(5):60-69.

\* cited by examiner

Fig. 3

Troubleshooting Tips

| Stoma Producing High Volume of Liquid Output | Leak at Barrier |
|---|---|
| • If using a 2-Piece Sur-Fit Natura® system, replace standard pouch with transparent high output pouch.<br>• If spout drain is not desired, cut off spout ending and use clamp supplied in the box. | • Repeat steps 1 - 6<br>• Make sure to follow proper accessory and system application<br>• Add belt if using a 2-Piece Sur-Fit Natura® system or 1-Piece Esteem® Plus Convex system. |
| Convexity | Odor |
| • If light convexity using a flat skin barrier and an Eakin® Cohesive seal is not successful, consult a WOC nurse<br>Caution:<br>• Convexity creates a gentle pressure around the stoma to push stoma forward.<br>• Do not use a convex skin barrier if surgery within past 10 days without consulting a WOC nurse.<br>• If past 10 days, a convex skin barrier may be used. | • If a 2-Piece system, check pouch to flange connection: clean or re-snap pouch to barrier connection<br>• Clean drainable tail area<br>• Check for leakes at barrier site |
| No WOC Nurse on Staff | Abdominal Tenderness |
| • Contact a ConvaTec WOC nurse at 1-800-422-8811 from Mon-Fri 8:30 am to 7:00 pm EST. | • If using a 2-Piece Sur-Fit Natura® system, add a Low Pressure Adaptor to avoid pressing down on belly to attach pouch.<br>• Or attach Sur-Fit Natura® pouch to the skin barrier before applying the whole system to the patient. |

Assessment 1 | Type Of Ostomy

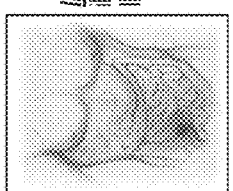

Colostomy: A surgically created opening into a portion of the colon (large intestine). Colostomy output varies from liquid to formed stool, based upon the location of the ostomy within the colon.

Choose appropriate management options on ostomy management plan:
1    2
(Consider option 3 if output is liquid.)

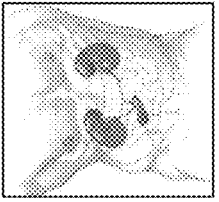

Ileostomy: A surgically created opening into the ileum (portion of the small intestine). Ileostomy output varies from pasty to liquid stool.

Choose appropriate management options on ostomy management plan:
1
(Option 2 is a personal choice.
Consider options 3 or 11 if output is liquid and/or high volume.)

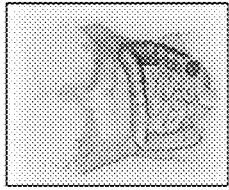

Urostomy: A surgically created opening into a portion of the urinary tract. Stomal ouput is urine. Urostomies can be created either by a direct opening into a portion of the urinary tract (ie, ureterostomy, vesicostomy) or by diverting the urine away from the bladder through a piece of intestine (ie, ileal conduit or colon conduit).

Choose appropriate management options on ostomy management plan:
3

FIG. 10

Assessment 3 | Stoma Type

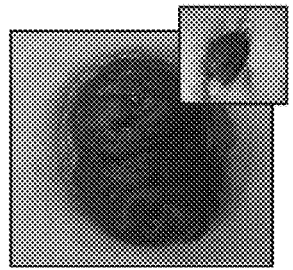

*End Stoma:* An end stoma is constructed by dividing the bowel and bringing out the proximal end to the skin surface as a single stoma.³

Choose appropriate management options:
7

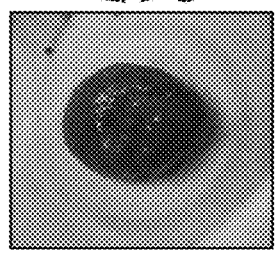

*Loop Stoma:* A loop stoma is constructed by bringing a loop of bowel to the abdominal surface and then opening the anterior wall of the bowel to provide fecal or urinary diversion.⁴ A rod is placed beneath the bowel in order to support the loop of intestine. Catheters can be used as an alternate to commercially available ostomy rods (also known as bridges).³

Choose appropriate management options:
7

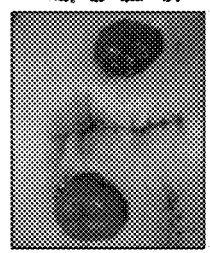

*Double-Barrel Stoma:* An doubel-barrel stoma is constructed when the bowel is divided and both the proximal and distal ends are brought to the skin surface as two separate stomas.⁴

Choose appropriate management options:
8

Fig. 12

Assessment 6 | Abdominal Contour
Abdominal contour can help determine an appropriate pouching system. The abdomen should be assessed while the patient is supine, sitting, and standing to determine if positional changes result in major changes in the abdominal contour. Changes have the potential to interfere with the effectiveness of the seal between the skin barrier and the peristomal skin.

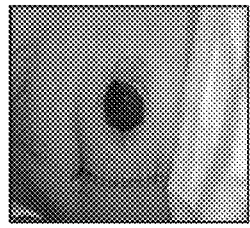

Flat and firm abdomen

*Choose appropriate management options:*
*9   10*
*(Consider option 11 if options do not provide secure optimal wear time.)*

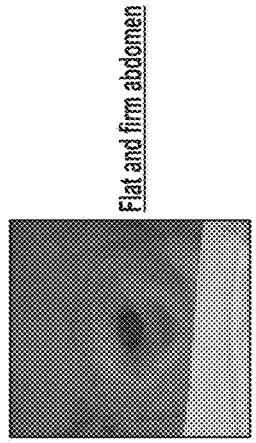

Soft and flaccid abdomen

*Choose appropriate management options:*
*11*
*(Consider options 9-10 if option does not provide secure optimal wear time.)*

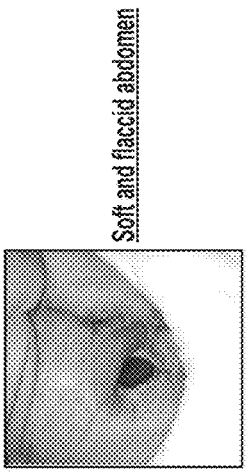

Round, protruding abdomen

*Choose appropriate management options:*
*9   10*
*(Consider option 11 if options do not provide secure optimal wear time.)*

Fig. 15

Assessment 7 | Level Pouching Surface
The area surrounding the stoma where the skin barrier will adhere is also known as the peristomal plane.⁷ The pouching surface area should be assessed while the patient is supine, sitting, and standing to determine pouching surface changes that could potentially interfere with the effectiveness of the skin barrier to peristomal skin seal.

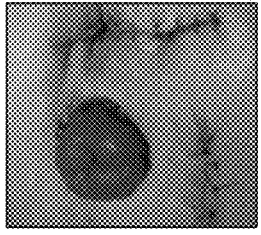

Level Pouching Surface: Minimal shifts in the peristomal plane in the supine, sitting, and standing positions.⁷

*Choose appropriate management options:*
*15*

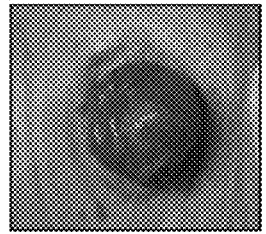

Stoma in a Skin Fold: Uneven areas within the peristomal plane need to be managed in order to achieve a level pouching surface.⁷

*16   17   18*

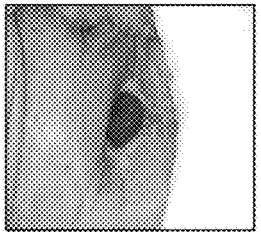

Pouching Surface Near Incisions

*Choose appropriate management options:*
*16   17   18   19*

Fig. 16

Assessment 8 | Presence/Absence of Devices
Temporary devices are often placed during surgery. Special precautions must be taken in order to prevent undue tension or potential dislodgement of the device, regardless of which management options are chosen.

Loop rods or stoma bridges are constructed by bringing a loop of bowel to the abdominal surface and making a transverse opening to provide fecal or urinary diversion.[4] A rod is placed beneath the bowel in order to support the loop of intestine. Catheters may be used as an alternative to commercially available ostomy rods (also known as bridges).[3] Surgically placed rods should only be removed when ordered by a physician.

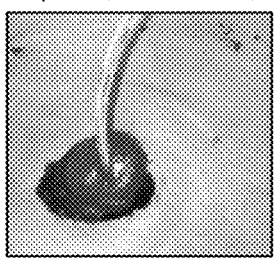

Ureteral stents are placed post urinary diversion surgery to maintain patency and protect the anastamosis of the ureters in the bowel segment. Typically, they are left in place for 5-7 days and should only be removed when ordered by a physician.[9] A variety of catheters may be used during surgery as alternatives to stents.

*Choose appropriate management options:*
21

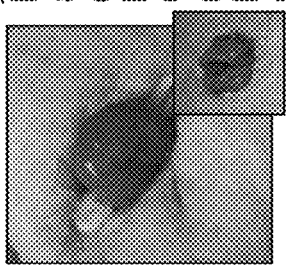

*Choose appropriate management options:*
20

Fig. 17

Assessment 9 | Presence/Absence Stoma Complications
An evaluation of peristomal planes will help determine an appropriate pouching system. The pouching surface area needs to be observed while the patient is supine, sitting, and standing to determine pouching surface changes that could potentially interfere with the effectiveness of the seal.

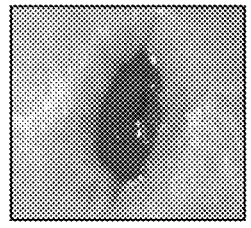

A parastomal hernia is a defect in the abdominal fascia that allows the intestine to bulge into the parastomal area.10

Choose appropriate management options:
22  23  24  25  26  27  28  29  30  31  32  33  34  35

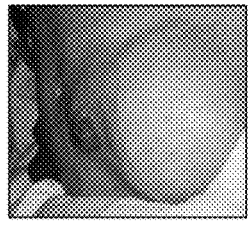

A stomal prolapse is a telescoping of the intestine through the stoma.10

Choose appropriate management options:
22  23  24  25  26  27  28  29  30  31  32  33  34  35  39

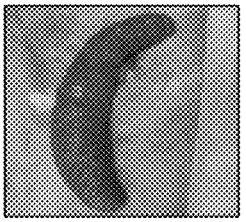

A retracted stoma is the disappearance of normal stoma protrusion in line with or below skin level.10

Choose appropriate management options:
22  23  24  27  28  29  30  31  32  35

Fig. 18

Assessment 9 | Presence/Absence Stoma Complications (cont'd)
An evaluation of peristomal planes will help determine an appropriate pouching system. The pouching surface area needs to be observed while the patient is supine, sitting, and standing to determine pouching surface changes that could potentially interfere with the effectiveness of the seal.

Stoma stenosis is an impairment of output due to narrowing or contracting of the stoma tissue at skin or fascia level. 10

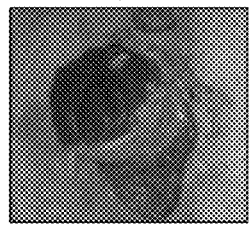

*Choose appropriate management options:*
22  23  24  27  28  29  30  31  32  33  34  35

Stoma necrosis is death of the stomal tissue resulting from impaired blood flow. 10

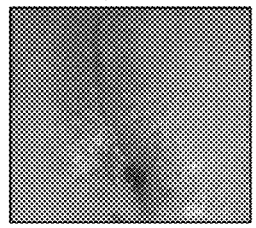

*Choose appropriate management options:*
22  23  24  28  29  30  31  32  34  35

Mucocutaneous separation is the detachment of stomal tissue from the surrounding peristomal skin. 10

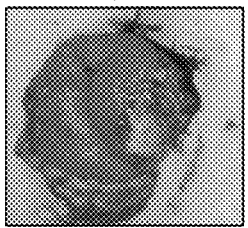

*Choose appropriate management options:*
22  23  24  28  29  30  31  32  34  35  36  37

Fig. 19

Assessment 11 | Presence/Absence of Peristomal Skin Complications (cont'd)

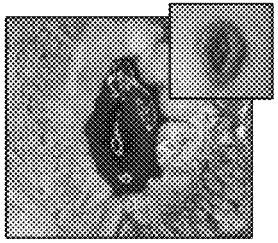

Pyoderma Gangrenosum is an ulcerative skin condition of unknown etiology occurring around a stoma.[10] Lesions are usually painful with red-to-purple margins.

Choose appropriate management options:
39  40  41  44  45  46  48  51  52

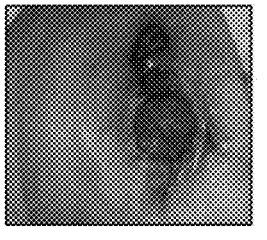

A Pseudoverrucous lesion is a wart-like lesion in the peristomal area related to chronic moisture exposure and irritation.[10]

Choose appropriate management options:
39  40  41  44  45  46  47  48  51  52

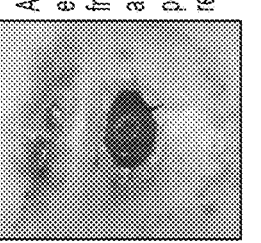

A peristomal pressure ulcer is loss of peristomal epidermis secondary to skin trauma[10] that results from pressure, friction, or shear, such as from abrasive cleaning technique, convexity, ill-fitting pouching system, ostomy belts, or improper removal of system.

Choose appropriate management options:
39  40  43  44  45  46  48  51  52

Fig. 23

[Head] [Feet — Head]
Patient Sitting
Enlarge Photos
Replay Intro

[Feet]
Patient Supine

CLINICAL INFORMATION for SCENARIO 1 of 7
Demographics:... 67-year-old female
Surgery:............ End colostomy, created 5 years ago
Diagnosis:......... Colon cancer
Stoma:.............. Protruding - 1 1/2 inch
                    Shape - round, diameter 1 1/4 inch
                    Other - Parastomal protrusion fluctuates dependent upon patient position
Abdomen:......... Round and protruding when patient in sitting position
Output:............. Soft and pasty stool, 2-3 times a day
Peristomal skin: Intact
Other:............... No visual, dexterity or cognitive issues Assessment 1: Type of Ostomy

1.A. *Select the type of ostomy this patient has.*
*Refer to Clinical Information box and Details and Definitions.*

- ☑ Colostomy
- ○ Ileostomy
- ○ Urostomy

View ✓ Full Algorithm

◁ Go Back

✎ Write Comments

▷ SUBMIT

Fig. 24B

✓ ALGORITHM | 📖 DETAILS AND DEFINITIONS

1.B. Details and Definitions

Management Options

1. DRAINABLE POUCH: A pouch with an opening at the bottom that is wide enough to empty solid stool. These pouches have two options for tail closures. 1) A detachable tail clamp is separate from the pouch. The patient should have enough hand strength to securely close the clamp. 2) An integrated tail closure for patients who prefer this option or if they have dexterity issues. Recommended for solid to semi-solid stool, or liquid stool that has a lot of particulate matter. Not recommended for purely liquid stool or urine.

2. CLOSED-END POUCH: A pouch without an opening or clamp at the bottom (also known as a non-drainable pouch). Recommended for solid to semi-solid stool; Not recommended for liquid stool or urine.

3. UROSTOMY POUCH: A pouch with a spout (tap/spigot) at the bottom to drain output. Recommended for urine or liquid stool with very little particulate matter. Not recommended for solid stool or liquid stool that has a lot of particulate matter.

Fig. 25A

CLINICAL INFORMATION for SCENARIO 1 of 7

Demographics:... 67-year-old female
Surgery:.......... End colostomy, created 5 years ago
Diagnosis:........ Colon cancer
Stoma:............ Protruding - 1 1/2 inch
   Shape - round, diameter 1 1/4 inch
   Other - Parastomal protrusion fluctuates dependent upon patient position
Abdomen:......... Round and protruding when patient in sitting position
Output:............ Soft and pasty stool, 2-3 times a day
Peristomal skin: Intact
Other:.............. No visual, dexterity or cognitive issues Assessment 2: Type and Volume of Output 2.A. Select the type and volume of output this patient has.
Refer to Clinical Information box and Details and Definitions.

Stool:
- ◯ Liquid
- ◯ Semi-liquid (liquid to pasty)
- ☑ Semi-formed (pasty-to-soft or oatmeal consistency)
- ◯ Formed
- ◯ Urine
- ◯ No output

Fig. 26B

✓ ALGORITHM | 📖 DETAILS AND DEFINITIONS

3.A. Details and Definitions

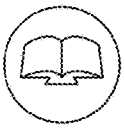
END STOMA: An end stoma is constructed by dividing the bowel and bringing out the proximal end to the skin surface as a single stoma.[3]

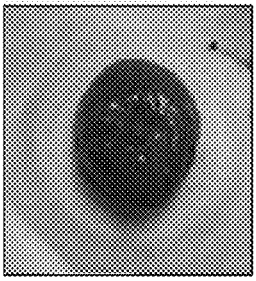
LOOP STOMA: A loop stoma is constructed by bringing a loop of bowel to the abdominal surface and then opening the anterior wall of the bowel to provide fecal or urinary diversion.[4] A rod temporarily is placed beneath the bowel in order to support the loop of intestine. Catheters can be used as an alternative to commercially available ostomy rods (also known as bridges).[3]

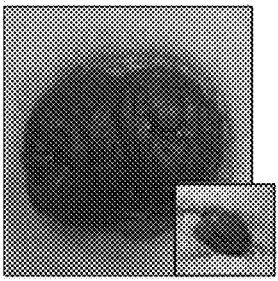
DOUBLE-BARREL STOMA: A double-barrel stoma is constructed when the bowel is divided and both the proximal and distal ends are brought to the skin surface as two separate stomas.[4]

Fig. 28A

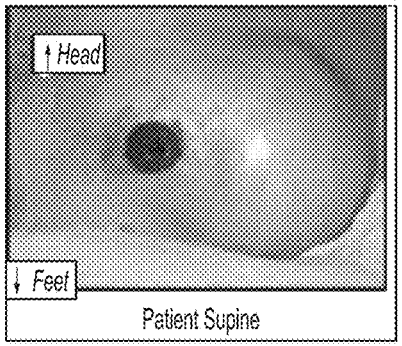

CLINICAL INFORMATION for SCENARIO 1 of 7

Demographics:... 67-year-old female
Surgery:............ End colostomy, created 5 years ago
Diagnosis:......... Colon cancer
Stoma:.............. Protruding - 1 1/2 inch
  Shape - round, diameter 1 1/4 inch
  Other - Parastomal protrusion fluctuates dependent upon patient position
Abdomen:.......... Round and protruding when patient in sitting position
Output:............... Soft and pasty stool, 2-3 times a day
Peristomal skin: Intact
Other:................ No visual, dexterity or cognitive issues Assessment 3: Type of Stoma 3.A  *Select the type of stoma this patient has.*
     *Refer to Clinical Information box and Details and Definitions.*

☑ End Stoma

◯ Loop Stoma

◯ Double-Barrel Stoma

View
Full Algorithm

Go Back

Write Comments

SUBMIT

Fig. 28B

✓ ALGORITHM | 📖 DETAILS AND DEFINITIONS

3.B. Details and Definitions

Management Options

7. SPECIAL CONSIDERATION FOR A LOOP OSTOMY SUPPORT DEVICE: If a loop ostomy support device is in place, the skin barrier should accomodate the device. If loop ostomy rod support is not sutured to skin, the skin barrier may be gently slid underneath the rod. Caution should be exercised at all times to avoid dislodging loop ostomy support device (i.e.: loop osotomy rod, red rubber catheter).

8. SPECIAL CONSIDERATION FOR A DOUBLE BARREL STOMA: When a double barrel stoma is created, the functioning end is called the proximal stoma and the non-functioning end is called the distal stoma or mucus fistula. The mucous fistula may temporarily drain fecal output and/or mucous. Ideally, the separation between stomas will be approximately 3". Both stomas may be pouched independently. Optionally, both stomas may be included in one pouch of the skin barrier surface will accomodate them.

CLINICAL INFORMATION for SCENARIO 1 of 7
Demographics:.. 67-year-old female
Surgery:............ End colostomy, created 5 years ago
Diagnosis:......... Colon cancer
Stoma:.............. Protruding - 1 1/2 inch
      Shape - round, diameter 1 1/4 inch
      Other - Parastomal protrusion fluctuates dependent upon patient position
Abdomen:......... Round and protruding when patient in sitting position
Output:............. Soft and pasty stool, 2-3 times a day
Peristomal skin: Intact
Other:............... No visual, dexterity or cognitive issues Assessment 4: Stoma Profile
(ie, the degree of stomal protrusion from skin level)

4.A. *Select the stoma profile this stoma has.*
     *Refer to Clinical Information box and Details and Definitions.*

○ Ideal Stoma

☑ Long Stoma

○ Flush/Retracted Stoma

Fig. 30B

✓ ALGORITHM | 📖 DETAILS AND DEFINITIONS

4.B. Details and Definitions

Management Options

9. ONE-PIECE POUCHING SYSTEM: In one-piece pouching systems, the skin barrier and pouch are attached together. Recommended for ease of application- particularly for patients with poor vision or dexterity, post-operatively and when there is need for a more flexible skin barrier than a two-piece system. It may have a lower profile. Not recommended for patients who want to switch between different pouches (e.g., drainable and closed-end), or for whom easy stoma access is necessary.

10. TWO-PIECE POUCHING SYSTEM: In two-piece pouching systems with flanges, the skin barrier and pouch are separate, but each has a semi-rigid or adhesive ring to attach the two parts. Recommended for patients with no vision or dexterity issues, for patients who want to switch between different pouches (e.g., drainable and closed-end) or post-operatively (when an adaptor is used to reduce pressure on abdomen or the two pieces are connected before applying). Not recommended when there is a need for a more flexible skin barrier.

11. CONVEX POUCHING SYSTEM: A skin barrier that is curved toward the abdomen to push inward around the stoma and peristomal skin, making the stoma protrude further. Not recommended when peristomal skin is not healed or not approximated or detached from the stoma. Not recommended when ulcerations are present. Recommended for use with flush or retracted stomas, flaccid abdomens, and when peristomal creases, skin folds or wrinkles are present. Not recommended for use with a protruding stoma or firm flat abdomen. *Monitor closely to ensure pressure ulcerations do not develop.

✓ ALGORITHM | 📖 DETAILS AND DEFINITIONS

5.B. Details and Definitions

Management Options

12. MOLDABLE SKIN BARRIER: A barrier that adheres to the skin and has a starter hole that is molded using the thumbs and fingers to match the size and shape of the stoma. The molding action creates a roll of adhesive that will hug the wall of the stoma so that the skin is not exposed. No cutting or pattern making is necessary with this barrier. Paste and washers are not generally needed with moldable barriers. Recommended for all stoma types, immediately after surgery and beyond, per the patient's preference. Also recommended for patients with visual, dexterity or cognitive issues or allergies to paste or other accessories. Not recommended for patients with a stoma size greater than 2 1/8 inch.

13. CUT-TO-FIT SKIN BARRIER: A barrier that adheres to the skin and has a small starter hole that the user will cut to a larger opening to match the shape of the stoma. Usually, a pattern mirroring the stoma shape is made and then the skin barrier is cut with rounded scissors to match the pattern, allowing for minimal peristomal skin exposure. Jagged cutting edges should be smoothed to avoid lacerations of the stoma. Paste or accessories products should be used to eliminate any exposed skin around the stoma. Recommend for all stoma shapes, immediately after surgery or beyond, per the patient's preference. Not recommended for patients with visual, dexterity or cognitive issues.

14. PRE-CUT SKIN BARRIER: A barrier that adheres to the skin and has a stoma opening already cut to a specific stoma diameter. Minimal or no cutting is needed. These barriers should closely match the stoma size and shape, allowing for minimal peristomal skin exposure to stool or urine. Paste or accessories products should be used to eliminate any exposed skin around the stoma.

Fig. 33A

 ALGORITHM  DETAILS AND DEFINITIONS

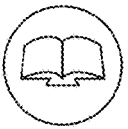

6.A. Details and Definitions

ABDOMINAL CONTOUR can help determine an appropriate pouching system. The abdomen should be assessed while the patient is supine, sitting, and standing to determine if positional changes result in major changes in the abdominal contour. Changes have the potential to interfere with the effectiveness of the seal between the skin barrier and the peristomal skin.

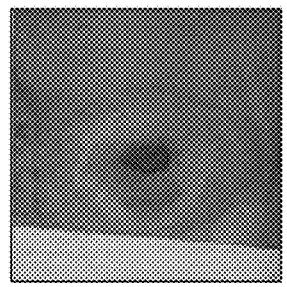 FLAT AND FIRM ABDOMEN

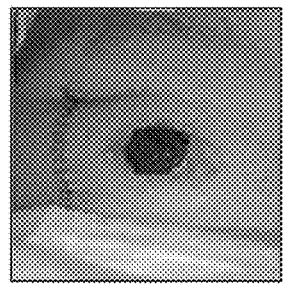 ROUND, PROTRUDING ABDOMEN

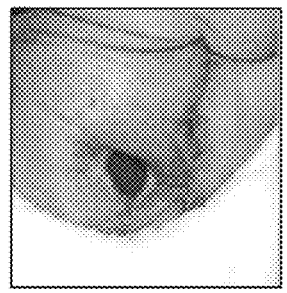 SOFT AND FLACCID ABDOMEN

| ✓ ALGORITHM | 📖 DETAILS AND DEFINITIONS |

6.B. Details and Definitions

Management Options

CHOICES BELOW ARE THE SAME AS ASSESSMENT 4.
When completing this assessment, consider your responses to Assessment 4 and reconsider your choices, if so desired.

9. ONE-PIECE POUCHING SYSTEM: In one-piece pouching systems, the skin barrier and pouch are attached together. Recommended for ease of application- particularly for patients with poor vision or dexterity, post-operatively and when there is need for a more flexible skin barrier than a two-piece system. It may have a lower profile. Not recommended for patients who want to switch between different pouches (e.g., drainable and closed-end), or for whom easy stoma access is necessary.

10. TWO-PIECE POUCHING SYSTEM: In two-piece pouching systems with flanges, the skin barrier and pouch are separate, but each has a semi-rigid or adhesive ring to attach the two parts. Recommended for patients with no vision or dexterity issues, for patients who want to switch between different pouches (e.g., drainable and closed-end) or post-operatively (when an adaptor is used to reduce pressure on abdomen or the two pieces are connected before applying). Not recommended when there is a need for a more flexible skin barrier.

11. CONVEX POUCHING SYSTEM: A skin barrier that is curved toward the abdomen to push inward around the stoma and peristomal skin, making the stoma protrude further. Recommended for use with flush or retracted stomas, flaccid abdomens, and when peristomal creases, skin folds or wrinkles are present. Not recommended for use with a protruding stoma or firm flat abdomen. *Monitor closely to ensure pressure ulcerations do not develop.

Fig. 35A

 ALGORITHM     DETAILS AND DEFINITIONS

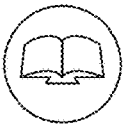

7.B. Details and Definitions

Management Options

Several options (accessory products) are available that will help enhance the skin barrier to peristomal skin seal when there are irregularities such as skin folds or creases in the pouching surface.

15. NO ACCESSORY PRODUCTS REQUIRED

16. SKIN BARRIER PASTE: is used to fill in uneven areas. It is placed as caulking around the cut edge of the solid skin barrier to prevent an undermining of the seal by stool or urine between the skin barrier and the peristomal skin. Recommended for use with cut-to-fit or pre-cut skin barriers to protect peristomal skin. Not recommended for patients with allergies/sensitivities or directly on broken peristomal skin.

17. SKIN BARRIER WASHERS/SEALS: are constructed of solid skin barrier material, and have no laminating film on top. These can be molded into various shapes to mirror the image of the pouching surface, and can also add mild convexity to a pouching system. They can be applied directly to the skin or added to the skin barrier. Recommended for use with cut-to-fit or pre-cut skin barriers to protect peristomal skin or when mild convexity is desired. Not recommended for patients with allergies/sensitivities.

18. SKIN BARRIER STRIPS: are constructed of solid skin barrier material in various lengths and thicknesses. They are used to fill an uneven area and provide an additional skin barrier around the stoma. Recommended for use when creases or folds in the pouching surface must be addressed to create a level pouching surface. Not recommended for patients with allergies/sensitivities.

19. PROTECT THE SURGICAL INCISION FROM CONTAMINATION: by stool or urine by removing the pouching system in a direction away from the incision. Assure a secure skin barrier seal at all times to help prevent leakage of effluent on the incision area.

 ALGORITHM  DETAILS AND DEFINITIONS

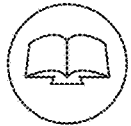

8.A. Details and Definitions

Temporary devices are often placed during surgery. Special precautions must be taken in order to prevent undue tension or potential dislodgement of the device, regardless of which management options are chosen.

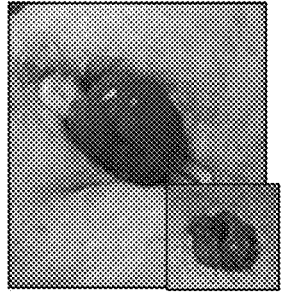

LOOP RODS
Loop rods or stoma bridges are constructed by bringing a loop of bowel to the abdominal surface and making a transverse opening to provide fecal or urinary diversion.[4] A rod is placed beneath the bowel in order to support the loop of intestine. Catheters may be used as an alternative to commercially available ostomy rods (also known as bridges).[3] Surgically placed rods should only be removed when ordered by a physician.

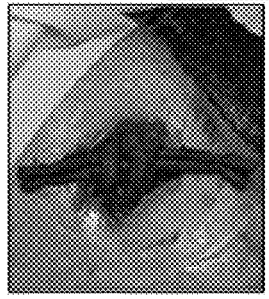

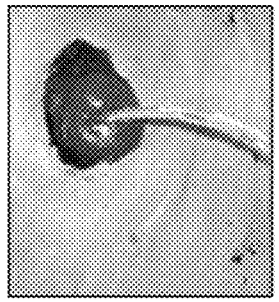

URETERAL STENTS
Ureteral stents are placed post urinary diversion surgery to maintain patency and protect the anastamosis of the ureters in the bowel segment. Typically, they are left in place for 5-7 days and should only be removed when ordered by a physician.[9] A variety of catheters may be used during surgery as alternatives to stents.

Fig. 38A

☑ ALGORITHM   📖 DETAILS AND DEFINITIONS

9.A. Details and Definitions

An evaluation of peristomal planes will help determine an appropriate pouching system. The pouching surface area needs to be observed while the patient is supine, sitting, and standing to determine pouching surface changes that could potentially interfere with the effectiveness of the seal.

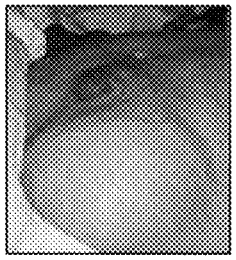

PARASTOMAL HERNIA
A parastomal hernia is a defect in the abdominal fascia that allows the intestine to bulge into the parastomal area.[10]

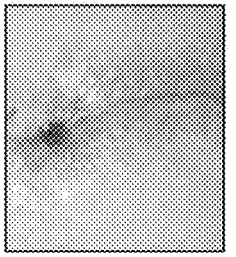

STOMA STENOSIS
Stoma stenosis is an impairment of output due to narrowing of contracting of the stoma tissue at skin or fascia level.[10]

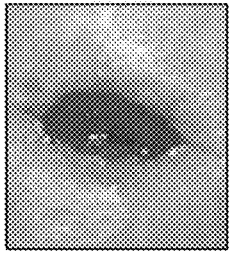

FLUSH/RETRACTED STOMA
A flush stoma is one that is at skin level.[5] Stomas that are below skin level are considered retracted.

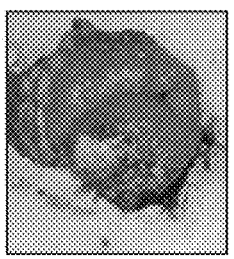

STOMA NECROSIS
Stoma necrosis is death of the stomal tissue resulting from impaired blood flow.[10]

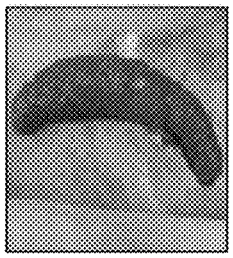

STOMAL PROLAPSE
A stomal prolapse is a telescoping of the intestine through the stoma.[10]

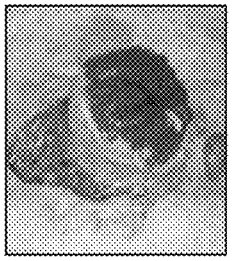

MUCOCUTANEOUS SEPARATION
Mucocutaneous separation is the detachment of stomal tissue from the surrounding peristomal skin.[10]

Fig. 39A

☑ ALGORITHM | 📖 DETAILS AND DEFINITIONS

9.B. Details and Definitions

Management Options

22. MODIFY OPENING OF SKIN BARRIER: The opening of the skin barrier may need to be altered if: 1) stomal complications are present such as a hernia or prolapse, 2) peristomal complications, arising from chronic leakage, are present such as irritant dermatitis 3) the swelling subsides after surgery and the stoma size and shape is established or 4) stoma necrosis is present and the necrotic/dead tissue sloughs.
    Re-measure skin barrier size and shape; choose smaller or larger skin barrier size and pouching system as needed. In general, a hernia or prolapse may require a larger skin barrier and opening while a smaller opening in the skin barrier is needed when irritant dermatitis, post-operative swelling subsides, or necrotic tissue sloughs off.

23. INCREASE FLEXIBILITY: CONSIDERATION: If the patient is wearing a two-piece pouching system with a rigid ring, a one-piece pouching system may provide more flexibility and a more secure seal between the skin barrier and the skin. This may be desired when a hernia is present, for example.

24. TWO-PIECE POUCHING SYSTEM: (same as option 10) In two-piece pouching systems with flanges, the skin barrier and pouch are separate, but each has a semi-rigid or adhesive ring to attach the two parts. Recommended for patients with no vision or dexterity issues, for patients who want to switch between different pouches (e.g., drainable and closed-end) or post-operatively (when an adaptor is used to reduce pressure on abdomen or the two pieces are connected before applying). Not recommended when there is a need for a more flexible skin barrier.

25. HERNIA SUPPORT BELTS: are available in several widths, based upon the patient's abdominal musculature and size of hernia. They are made from an elastic material that provides support for the hernia, and have a reinforced opening that allows the pouch to be unrestricted. A hernia support belt should be applied when the patient is lying down. Consult with a WOC Nurse, ostomy supplier or manufacturer for ordering information.

26. HERNIA SUPPORT BELT WITH PROLAPSE FLAP: As above (option 25), this belt has an additional elastic flap that is secured over the pouch in an attempt to prevent a prolapsed stoma from further enlarging. Consult with a WOC Nurse, ostomy supplier or manufacturer for ordering information.

27. USE CONVEXITY WITH CAUTION: The inappropriate use of

Fig. 40A

| ALGORITHM | DETAILS AND DEFINITIONS |

Assessment 1: Type of Ostomy
  Assessment: Colostomy
  Management Options: Drainable Pouch

Assessment 2: Type and Volume of Output
  Assessment: Semi-formed (pasty-to-soft or oatmeal consistency)
  Management Options: Regular-Wear Skin Barriers

Assessment 3: Stoma Type
  Assessment: End Stoma
  Management Options: Not Applicable

Assessment 4: Stoma Profile
  Assessment: Long Stoma
  Management Options: One-Piece Pouching System

Assessment 5: Stoma Shape
  Assessment: Round Stoma
  Management Options: Cut-to-fit Skin Barrier

Assessment 6: Abdominal Contour
  Assessment: Round and Protruding
  Management Options: One-Piece Pouching System

Assessment 7: Level Pouching Surface
  Assessment: Level
  Management Options: Skin Barrier Paste, Skin Barrier Washer/Seals

Assessment 8: Presence/Absence of Devices
  Assessment: No Device Present
  Management Options: Not Applicable

Assessment 9: Presence/Absence of Stoma Complications
  Assessment: Peristomal Hernia
  Management Options: Modify Opening of Skin Barrier, Increase Flexibility, Support Belts, Referral to a WOC Nurse, Referral to Surgeon, Resize Skin Barrier

Assessment 10: Peristomal Skin Assessment
  Lesion (L) Classification: No Lesion
  Location (T) Classification: Not Applicable

Assessment 11: Presence/Absence of Peristomal Skin Complications
  Assessment: No Complications
  Management Options: Not Applicable

METHODS AND SYSTEMS FOR OSTOMY CARE

CROSS-REFERENCE TO RELATED APPLICATIONS

This application claims the benefit of U.S. Application Ser. No. 61/765,629, filed Feb. 15, 2013, which is hereby incorporated by reference in its entirety.

BACKGROUND OF THE INVENTION

Ostomy care and education in U.S. hospitals typically consists of 3-4 postoperative visits by the specialty nurse (Wound Ostomy and Continence) if available at the facility. [5] When a specialty nurse is not available, ostomy education is provided by a staff nurse. [1,5] At discharge, ongoing teaching for the patient with an ostomy is transferred to the home healthcare agency or long-term care facility. [3,7] A majority of ostomy patient education now occurs in patients' homes or in long term care. [2] In 2008, WOC nurses reported spending 21% of their time devoted primarily to ostomy care, and 22% in 2012. [8,9] According to the WOCN®, only 9.9% of WOC nurses identify their primary practice setting as home care, and only 4.1% as long-term care. [9]

SUMMARY OF THE INVENTION

A majority of ostomy care is being provided by non-specialized clinicians or unskilled caregivers and family members. Patients with ostomies often state that staff nurses display a lack of confidence in both knowledge and skills related to ostomy care. [6] One of the most difficult challenges facing clinicians who care for individuals with an ostomy is selection of an appropriate pouching system, and correction of existing management-related problems. [2] For non-specialized clinicians unfamiliar with ostomy care and the vast array of different products available, this challenge can be intimidating. [1,2,7]

Safety and quality care are dependent on bedside decision makers utilizing the best possible research. [10] Since data indicate that non-specialized nurses are providing a substantial volume of ostomy care, a great need exists to provide these clinicians with an evidence-based instrument to guide decision making in selection of a safe pouching system.

In one aspect, disclosed herein are methods of administering an ostomy device or product to an individual in need thereof, the method comprising: assessing one or more of: skin adjacent an ostomy, topographical location of any peristomal lesion, stoma type, pouching surface, stoma devices present, and stoma complications to generate ostomy assessment information; applying an algorithm to the ostomy assessment information, the algorithm providing one or more ostomy management options; and administering an ostomy care device or product based on the one or more ostomy management options. In some embodiments, the ostomy management options comprise one or more of: a device recommendation, a product recommendation, an instruction, a treatment, consideration, and a caution. In further embodiments, a device recommendation comprises a plurality of device options. In further embodiments, a product recommendation comprises a plurality of product options. In still further embodiments, a device or product recommendation comprises no device or product. In some embodiments, the algorithm provides the one or more ostomy management options by matching ostomy assessment information to at least one ostomy care product or device. In some embodiments, each assessment is made by selecting a condition from a list of potential conditions. In some embodiments, assessing skin adjacent an ostomy comprises selecting one of: healthy skin, hyperemic lesion, erosive lesion, ulcerative lesion, ulcerative lesion with non-viable tissue, and proliferative lesion. In some embodiments, assessing topographical location of any peristomal lesion comprises selecting one of: upper right quadrant, lower right quadrant, lower left quadrant, upper left quadrant, and all quadrants. In some embodiments, assessing stoma type comprises selecting one of: flush, narrow oval, and other. In some embodiments, assessing pouching surface comprises selecting one of: soft and flaccid abdomen, stoma in crease or skin fold, pouching area near incision, and other. In some embodiments, assessing stoma devices present comprises selecting one of: rod or bridge, stent, and other. In some embodiments, assessing stoma complications comprises selecting one of: retracted stoma, hernia, prolapsed stoma, mucotaneous separation, dark stoma color, and other.

In another aspect, disclosed herein are computer-implemented systems comprising: a digital processing device comprising an operating system configured to perform executable instructions and a memory device; and a computer program including instructions executable by the digital processing device to create an interactive ostomy treatment guide comprising: a software module configured to receive ostomy assessment information, the assessment information comprising one or more of: condition of skin adjacent an ostomy, topographical location of any peristomal lesion, stoma type, pouching surface type, stoma devices present, and stoma complications; a software module configured to apply a treatment algorithm to the ostomy assessment information to generate an output; and a software module configured to display one or more ostomy management options based on the output. In some embodiments, the interactive ostomy treatment guide further comprises a software module configured to provide definitions of terms. In some embodiments, the interactive ostomy treatment guide further comprises a software module configured to provide exemplary photographs to support determination of ostomy assessment information. In some embodiments, the ostomy management options comprise one or more of: a device recommendation, a product recommendation, an instruction, a treatment, consideration, and a caution. In further embodiments, a device recommendation comprises a plurality of device options. In further embodiments, a product recommendation comprises a plurality of product options. In still further embodiments, a device or product recommendation comprises no device or product. In some embodiments, the algorithm provides the output by matching ostomy assessment information to at least one ostomy care product or device. In some embodiments, ostomy assessment information comprises a condition selected from a list of potential conditions. In some embodiments, skin adjacent an ostomy is selected from: healthy skin, hyperemic lesion, erosive lesion, ulcerative lesion, ulcerative lesion with non-viable tissue, and proliferative lesion. In some embodiments, topographical location of any peristomal lesion is selected from: upper right quadrant, lower right quadrant, lower left quadrant, upper left quadrant, and all quadrants. In some embodiments, stoma type is selected from: flush, narrow oval, and other. In some embodiments, pouching surface is selected from: soft and flaccid abdomen, stoma in crease or skin fold, pouching area near incision, and other. In some embodiments, stoma devices present is selected from: rod or bridge, stent, and other. In some embodiments, stoma complications is selected from: retracted stoma, hernia, prolapsed stoma, mucotaneous separation, dark stoma color, and other. In some embodiments, the treatment guide is implemented as a web application. In other embodiments, the treatment guide is implemented as a mobile application.

In another aspect, disclosed herein are non-transitory computer-readable storage media encoded with a computer program including instructions executable by a processor to create an interactive ostomy treatment guide comprising: a software module configured to receive ostomy assessment information, the assessment information comprising one or more of: condition of skin adjacent an ostomy, topographical location of any peristomal lesion, stoma type, pouching surface type, stoma devices present, and stoma complications; a software module configured to apply a treatment algorithm to the ostomy assessment information to generate an output; and a software module configured to display one or more ostomy care management options based on the output. In some embodiments, the interactive ostomy treatment guide further comprises a software module configured to provide definitions of terms. In some embodiments, the interactive ostomy treatment guide further comprises a software module configured to provide exemplary photographs to support determination of ostomy assessment information. In some embodiments, the ostomy management options comprise one or more of: a device recommendation, a product recommendation, an instruction, a treatment, consideration, and a caution. In further embodiments, a device recommendation comprises a plurality of device options. In further embodiments, a product recommendation comprises a plurality of product options. In still further embodiments, a device or product recommendation comprises no device or product. In some embodiments, the algorithm provides the output by matching ostomy assessment information to at least one ostomy care product or device. In some embodiments, ostomy assessment information comprises a condition selected from a list of potential conditions. In some embodiments, skin adjacent an ostomy is selected from: healthy skin, hyperemic lesion, erosive lesion, ulcerative lesion, ulcerative lesion with non-viable tissue, and proliferative lesion. In some embodiments, topographical location of any peristomal lesion is selected from: upper right quadrant, lower right quadrant, lower left quadrant, upper left quadrant, and all quadrants. In some embodiments, stoma type is selected from: flush, narrow oval, and other. In some embodiments, pouching surface is selected from: soft and flaccid abdomen, stoma in crease or skin fold, pouching area near incision, and other. In some embodiments, stoma devices present is selected from: rod or bridge, stent, and other. In some embodiments, stoma complications is selected from: retracted stoma, hernia, prolapsed stoma, mucotaneous separation, dark stoma color, and other. In some embodiments, the treatment guide is implemented as a web application. In other embodiments, the treatment guide is implemented as a mobile application.

In another aspect, disclosed herein are methods of administering an ostomy device or product to an individual in need thereof, the method comprising: assessing one or more of: skin adjacent an ostomy, topographical location of any peristomal lesion, stoma type, pouching surface, stoma devices present, and stoma complications; applying an algorithm to each assessment, the algorithm providing ostomy care guidance comprising one or more of: at least one ostomy management option, a consideration, at least one device recommendation, at least one product recommendation, an instruction, a treatment, and a caution; and administering an ostomy care device or product to the individual based on each ostomy care guidance. In some embodiments, the ostomy management options comprise one or more of: a device recommendation, a product recommendation, an instruction, a treatment, consideration, and a caution. In some embodiments, the algorithm provides the ostomy care guidance by matching ostomy assessment information to at least one ostomy care product or device.

In another aspect, disclosed herein are methods of administering an ostomy care device or product to an individual in need thereof, the method comprising: assessing type of ostomy, type and volume of output, stoma type, stoma profile, stoma shape, abdominal contour, levelness of pouching surface, stoma devices present, stoma complications, peristomal skin condition, and peristomal skin complications; applying an algorithm to each assessment, the algorithm providing ostomy care guidance comprising one or more of: at least one ostomy management option, a consideration, at least one device recommendation, at least one product recommendation, an instruction, a treatment, and a caution; and administering an ostomy care device or product to the individual based on each ostomy care guidance. In some embodiments, the algorithm provides the ostomy care guidance by matching ostomy assessment information to at least one ostomy care product or device. In some embodiments, the ostomy care guidance comprises about 1 to about 10 ostomy management options. In some embodiments, each assessment is made by selecting a condition from a list of potential conditions. In some embodiments, assessing type of ostomy comprises selecting one of: colostomy, ileostomy, and urostomy. In some embodiments, assessing type and volume of output comprises selecting one of: ascending to transverse colon output of mostly high-volume liquid stool, transverse to descending colon output of pasty-to-soft or oatmeal-consistency stool, sigmoid colon output similar to that of intact colon, early post-op ileum output of liquid-to-pasty stool at 1000-1800 ml/day, 6 months or more post-op ileum output of oatmeal-consistency stool, and urine output. In some embodiments, assessing stoma type comprises selecting one of: end stoma, loop stoma, and double-barrel stoma. In some embodiments, assessing stoma profile comprises selecting one of: ideal stoma, long stoma, and flush stoma. In some embodiments, assessing stoma shape comprises selecting one of: round stoma, irregular stoma, oval stoma, and mushroom-shaped stoma. In some embodiments, assessing abdominal contour comprises selecting one of: flat and firm abdomen, round and protruding abdomen, and soft and flaccid abdomen. In some embodiments, assessing levelness of pouching surface comprises selecting one of: level pouching surface, pouching surface near incisions, and stoma in a skin fold. In some embodiments, assessing stoma devices present comprises selecting one of: loop rod or stoma bridge and ureteral stent. In some embodiments, assessing stoma complications comprises selecting one of: parastomal hernia, retracted stoma, stromal prolapse, stoma stenosis, mucotaneous separation, and stoma necrosis. In some embodiments, assessing peristomal skin condition comprises selecting one of: hyperemic lesion, erosive lesion, ulcerative lesion, ulcerative lesion with non-viable tissue, and proliferative lesion. In some embodiments, assessing peristomal skin condition further comprises selecting one of: upper right quadrant, lower right quadrant, lower left quadrant, upper left quadrant, and all quadrants. In some embodiments, assessing peristomal skin complications comprises selecting one of: candidiasis, irritant contact dermatitis, folliculitis, allergic contact dermatitis, pesudoverrucous lesion, pyoderma gangrenosum, and peristomal pressure ulcer.

In another aspect, disclosed herein are computer-implemented systems comprising: a digital processing device comprising an operating system configured to perform executable instructions and a memory device; and a computer program including instructions executable by the digital processing device to create an interactive ostomy treatment guide comprising: a software module configured to receive an assessment of: type of ostomy, type and volume of output, stoma type, stoma profile, stoma shape, abdominal contour, levelness of pouching surface, stoma devices present, stoma complications, peristomal skin condition, and peristomal skin complications; a software module configured to apply a treatment algorithm to each assessment to generate an output; and a software module configured to display one or more ostomy management options based on the output. In some embodiments, the interactive ostomy treatment guide further comprises a software module configured to provide definitions of terms. In some embodiments, the interactive ostomy treatment guide further comprises a software module configured to provide exemplary photographs to support ostomy assessments. In some embodiments, the ostomy management options comprise one or more of: a device recommendation, a product recommendation, an instruction, a treatment, consideration, and a caution. In further embodiments, a device recommendation comprises a plurality of device options. In further embodiments, a product recommendation comprises a plurality of product options. In still further embodiments, a device or product recommendation comprises no device or product. In some embodiments, the algorithm provides the output by matching the assessment to at least one ostomy care product or device. In some embodiments, each assessment is made by selecting a condition from a list of potential conditions. In some embodiments, assessing type of ostomy comprises selecting one of: colostomy, ileostomy, and urostomy. In some embodiments, assessing type and volume of output comprises selecting one of: ascending to transverse colon output of mostly high-volume liquid stool, transverse to descending colon output of pasty-to-soft or oatmeal-consistency stool, sigmoid colon output similar to that of intact colon, early post-op ileum output of liquid-to-pasty stool at 1000-1800 ml/day, 6 months or more post-op ileum output of oatmeal-consistency stool, and urine output. In some embodiments, assessing stoma type comprises selecting one of: end stoma, loop stoma, and double-barrel stoma. In some embodiments, assessing stoma profile comprises selecting one of: ideal stoma, long stoma, and flush stoma. In some embodiments, assessing stoma shape comprises selecting one of: round stoma, irregular stoma, oval stoma, and mushroom-shaped stoma. In some embodiments, assessing abdominal contour comprises selecting one of: flat and firm abdomen, round and protruding abdomen, and soft and flaccid abdomen. In some embodiments, assessing levelness of pouching surface comprises selecting one of: level pouching surface, pouching surface near incisions, and stoma in a skin fold. In some embodiments, assessing stoma devices present comprises selecting one of: loop rod or stoma bridge and ureteral stent. In some embodiments, assessing stoma complications comprises selecting one of: parastomal hernia, retracted stoma, stromal prolapse, stoma stenosis, mucotaneous separation, and stoma necrosis. In some embodiments, assessing peristomal skin condition comprises selecting one of: hyperemic lesion, erosive lesion, ulcerative lesion, ulcerative lesion with non-viable tissue, and proliferative lesion. In some embodiments, assessing peristomal skin condition further comprises selecting one of: upper right quadrant, lower right quadrant, lower left quadrant, upper left quadrant, and all quadrants. In some embodiments, assessing peristomal skin complications comprises selecting one of: candidiasis, irritant contact dermatitis, folliculitis, allergic contact dermatitis, pesudoverrucous lesion, pyoderma gangrenosum, and peristomal pressure ulcer.

In another aspect, disclosed herein are non-transitory computer-readable storage media encoded with a computer program including instructions executable by a processor to create an interactive ostomy treatment guide comprising: a software module configured to receive an assessment of: type of ostomy, type and volume of output, stoma type, stoma profile, stoma shape, abdominal contour, levelness of pouching surface, stoma devices present, stoma complications, peristomal skin condition, and peristomal skin complications; a software module configured to apply a treatment algorithm to each assessment to generate an output; and a software module configured to display one or more ostomy management options based on the output. In some embodiments, the interactive ostomy treatment guide further comprises a software module configured to provide definitions of terms. In some embodiments, the interactive ostomy treatment guide further comprises a software module configured to provide exemplary photographs to support determination of ostomy assessment information. In some embodiments, the ostomy management options comprise one or more of: a device recommendation, a product recommendation, an instruction, a treatment, consideration, and a caution. In further embodiments, a device recommendation comprises a plurality of device options. In further embodiments, a product recommendation comprises a plurality of product options. In still further embodiments, a device or product recommendation comprises no device or product. In some embodiments, the algorithm provides the output by matching ostomy assessment information to at least one ostomy care product or device. In some embodiments, ostomy assessment information comprises a condition selected from a list of potential conditions. In some embodiments, skin adjacent an ostomy is selected from: healthy skin, hyperemic lesion, erosive lesion, ulcerative lesion, ulcerative lesion with non-viable tissue, and proliferative lesion. In some embodiments, topographical location of any peristomal lesion is selected from: upper right quadrant, lower right quadrant, lower left quadrant, upper left quadrant, and all quadrants. In some embodiments, stoma type is selected from: flush, narrow oval, and other. In some embodiments, pouching surface is selected from: soft and flaccid abdomen, stoma in crease or skin fold, pouching area near incision, and other. In some embodiments, stoma devices present is selected from: rod or bridge, stent, and other. In some embodiments, stoma complications is selected from: retracted stoma, hernia, prolapsed stoma, mucotaneous separation, dark stoma color, and other. In some embodiments, the treatment guide is implemented as a web application. In other embodiments, the treatment guide is implemented as a mobile application.

BRIEF DESCRIPTION OF THE DRAWINGS

Figure 3:
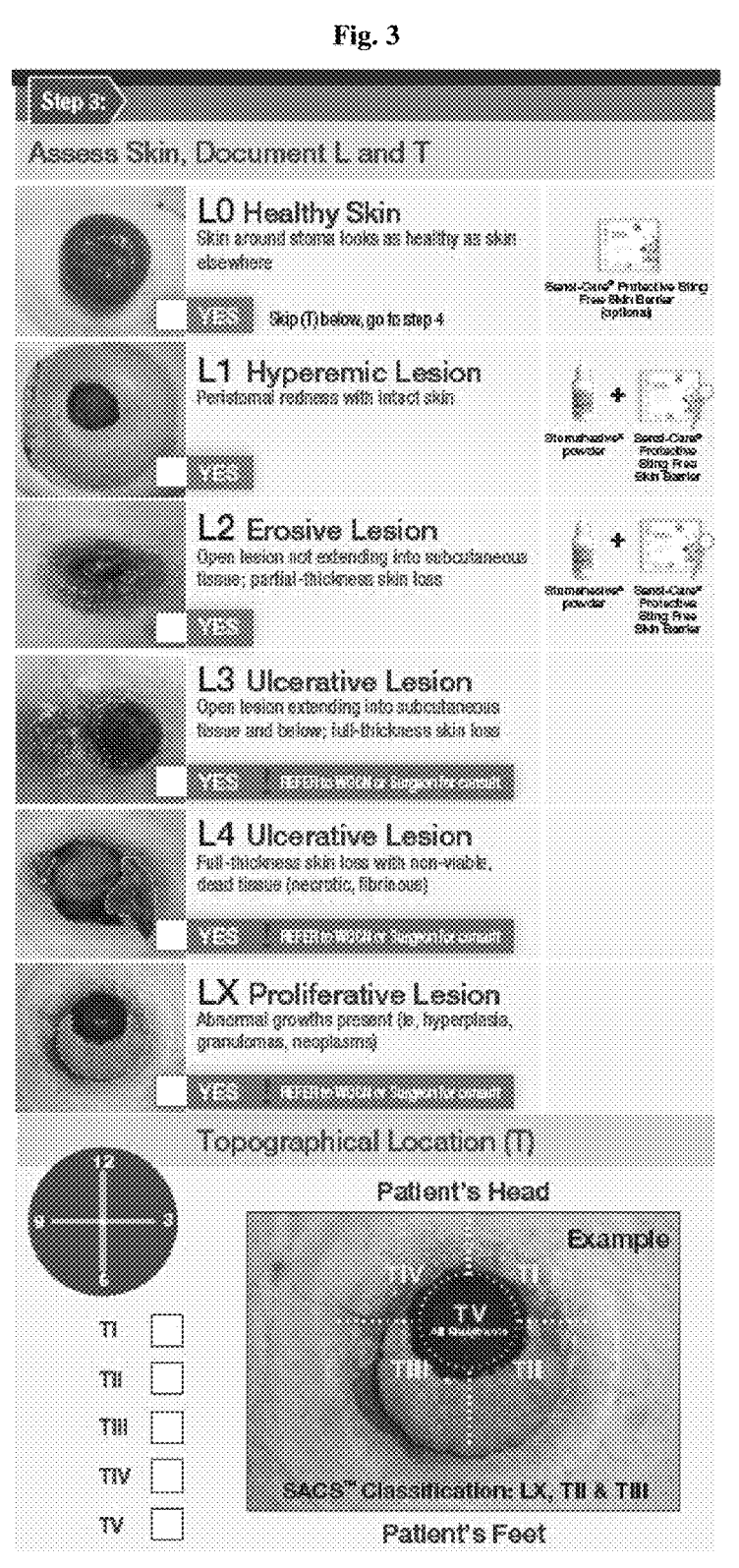

FIG. 3 shows a non-limiting example of a bedside tool for facilitating the methods described herein; in this case, a bedside tool including a checklist for assessing skin adjacent an ostomy and topographical location of any peristomal lesion present and applying an algorithm to match ostomy management options to the assessment information.

FIG. 8 shows a non-limiting example of a bedside tool for facilitating the methods described herein; in this case, a bedside tool including troubleshooting for common ostomy issues.

FIG. 9 shows a non-limiting example of a bedside tool for facilitating the methods described herein; in this case, a bedside tool including contact information for discharge support.

FIG. 10 shows a non-limiting example of an ostomy treatment algorithm; in this case, an algorithm matching assessments pertaining to type of ostomy with ostomy management options.

FIG. 12 shows a non-limiting example of an ostomy treatment algorithm; in this case, an algorithm matching assessments pertaining to stoma type with ostomy management options.

FIG. 15 shows a non-limiting example of an ostomy treatment algorithm; in this case, an algorithm matching assessments pertaining to abdominal contour with ostomy management options.

FIG. 16 shows a non-limiting example of an ostomy treatment algorithm; in this case, an algorithm matching assessments pertaining to levelness of pouching surface with ostomy management options.

FIG. 17 shows a non-limiting example of an ostomy treatment algorithm; in this case, an algorithm matching assessments pertaining to presence or absence of stoma devices with ostomy management options.

FIGS. 18-19 show non-limiting examples of an ostomy treatment algorithm; in this case, an algorithm matching assessments pertaining to presence or absence of stoma complications with ostomy management options.

FIGS. 22-23 show non-limiting examples of an ostomy treatment algorithm; in this case, an algorithm matching assessments pertaining to presence or absence of peristomal skin complications with ostomy management options.

FIGS. 24A and 24B shows a non-limiting example of an interactive tool for construct validation of an ostomy care algorithm using digital real-life clinical scenarios; in this case a tool presenting a GUI for selecting type of ostomy.

FIGS. 25A and 25B shows a non-limiting example of an interactive tool for construct validation of an ostomy care algorithm using digital real-life clinical scenarios; in this case a tool presenting a GUI for selecting an appropriate management option based on type of ostomy.

FIGS. 26A and 26B shows a non-limiting example of an interactive tool for construct validation of an ostomy care algorithm using digital real-life clinical scenarios; in this case a tool presenting a GUI for selecting type and volume of output.

FIGS. 28A and 28B shows a non-limiting example of an interactive tool for construct validation of an ostomy care algorithm using digital real-life clinical scenarios; in this case a tool presenting a GUI for selecting type of stoma.

Figure 29B:
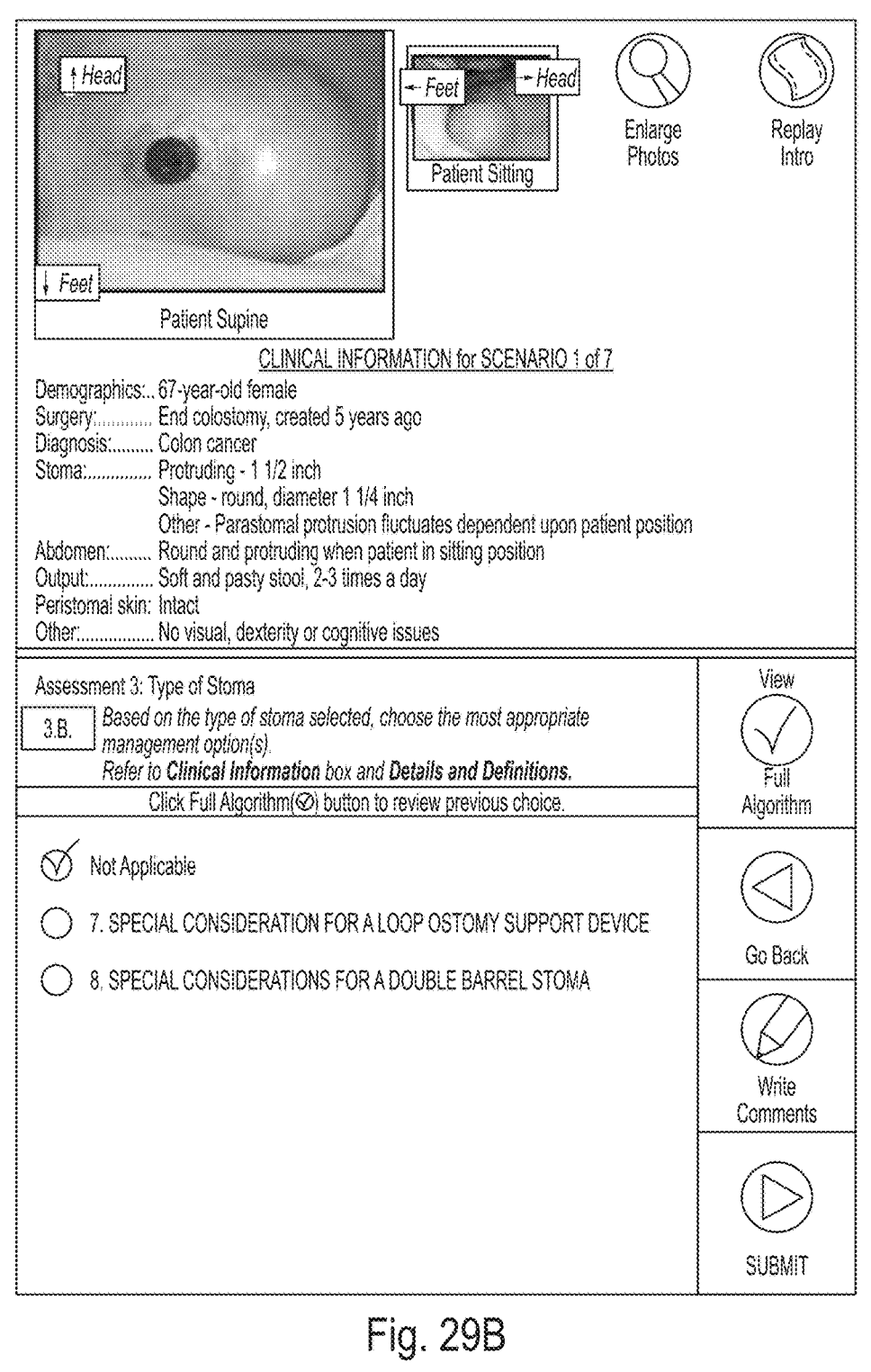

FIGS. 29A and 29B shows a non-limiting example of an interactive tool for construct validation of an ostomy care algorithm using digital real-life clinical scenarios; in this case a tool presenting a GUI for selecting an appropriate management option based on type of stoma.

FIGS. 30A and 30B shows a non-limiting example of an interactive tool for construct validation of an ostomy care algorithm using digital real-life clinical scenarios; in this case a tool presenting a GUI for selecting stoma profile.

FIGS. 31A and 31B shows a non-limiting example of an interactive tool for construct validation of an ostomy care algorithm using digital real-life clinical scenarios; in this case a tool presenting a GUI for selecting an appropriate management option based on stoma profile.

Figure 32B:
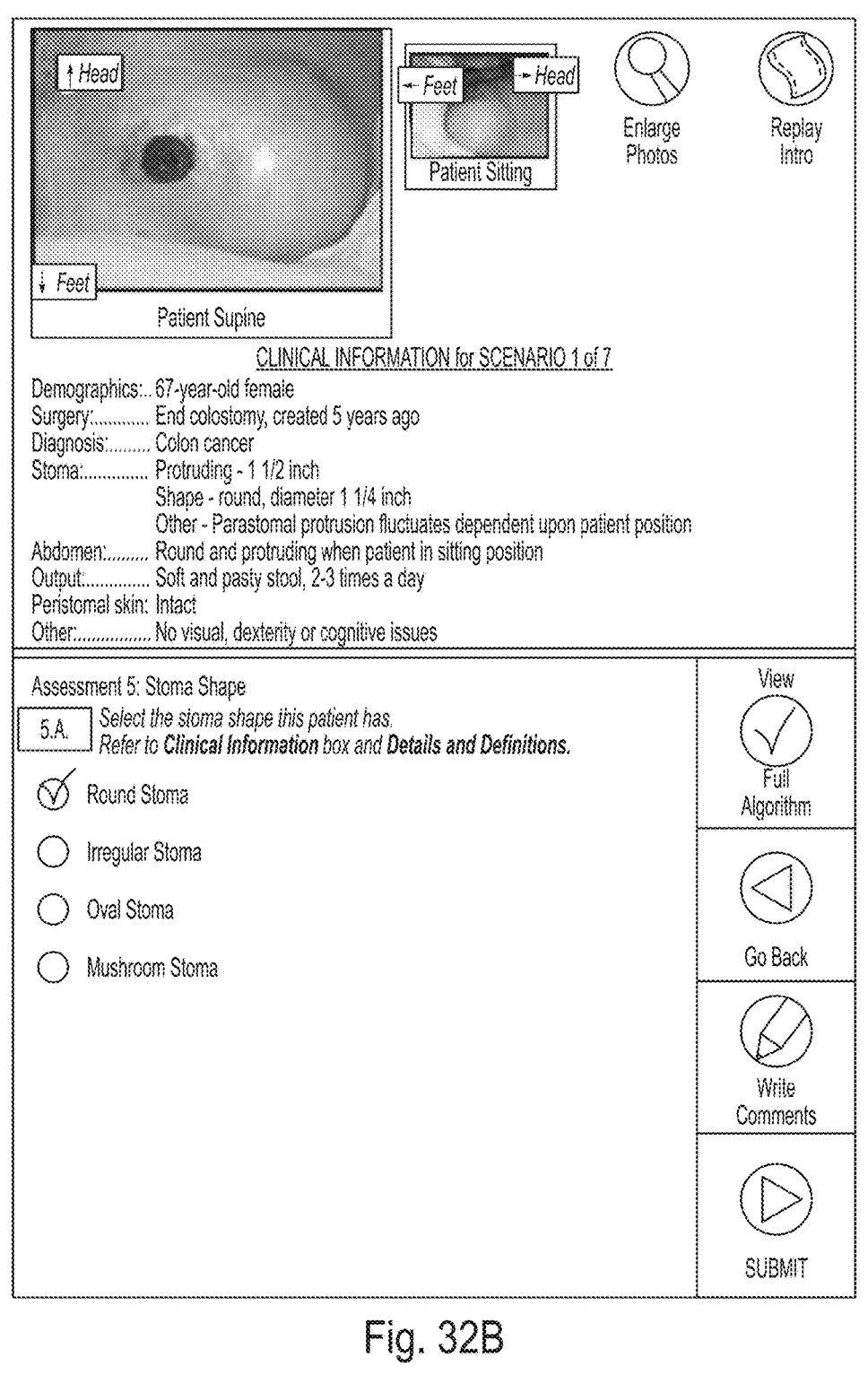

FIGS. 32A and 32B shows a non-limiting example of an interactive tool for construct validation of an ostomy care algorithm using digital real-life clinical scenarios; in this case a tool presenting a GUI for selecting stoma shape.

FIGS. 33A and 33B shows a non-limiting example of an interactive tool for construct validation of an ostomy care algorithm using digital real-life clinical scenarios; in this case a tool presenting a GUI for selecting an appropriate management option based on stoma shape.

Figure 34B:
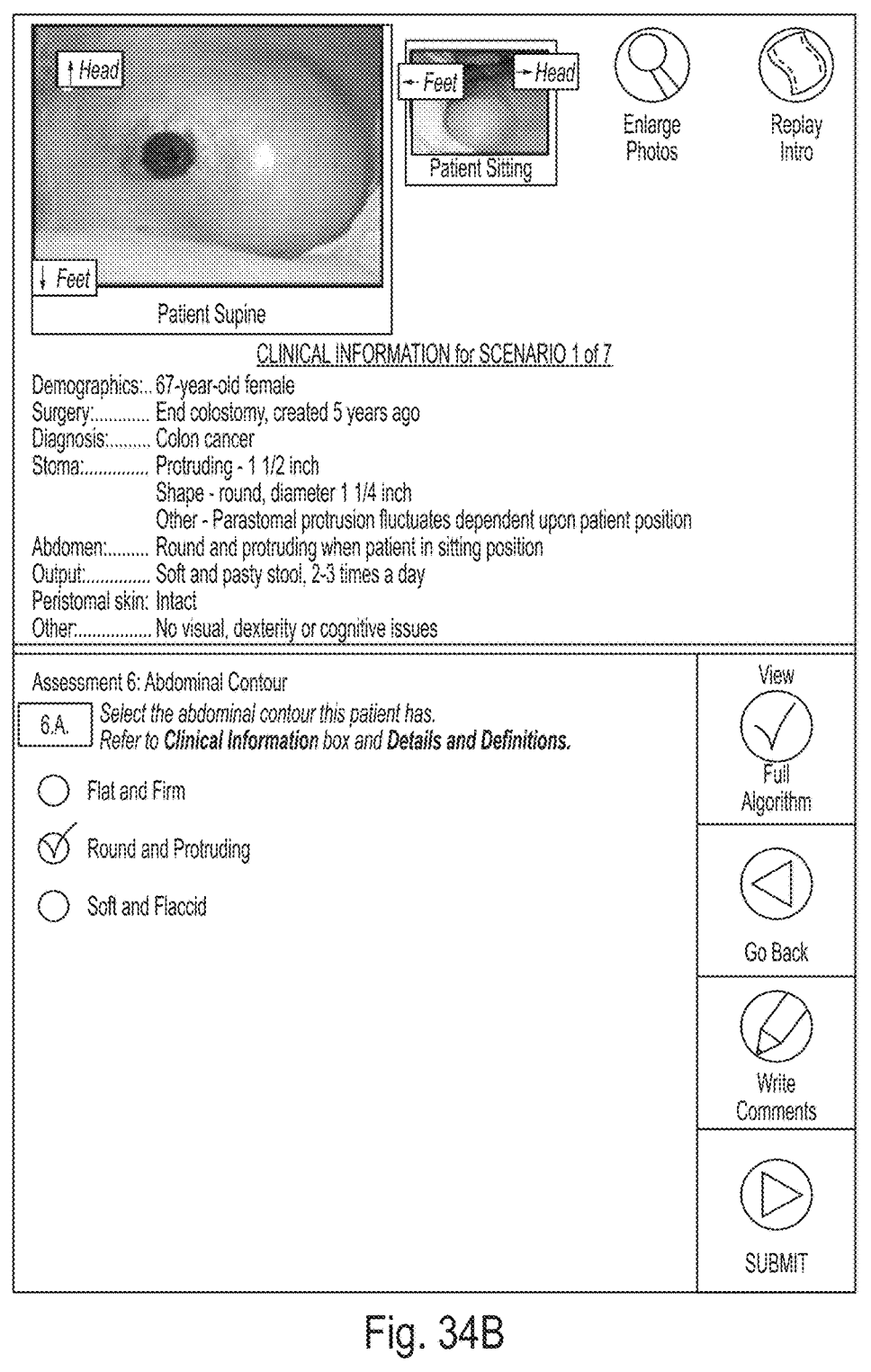

FIGS. 34A and 34B shows a non-limiting example of an interactive tool for construct validation of an ostomy care algorithm using digital real-life clinical scenarios; in this case a tool presenting a GUI for selecting abdominal contour.

FIGS. 35A and 35B shows a non-limiting example of an interactive tool for construct validation of an ostomy care algorithm using digital real-life clinical scenarios; in this case a tool presenting a GUI for selecting an appropriate management option based on abdominal contour.

Figure 37B:
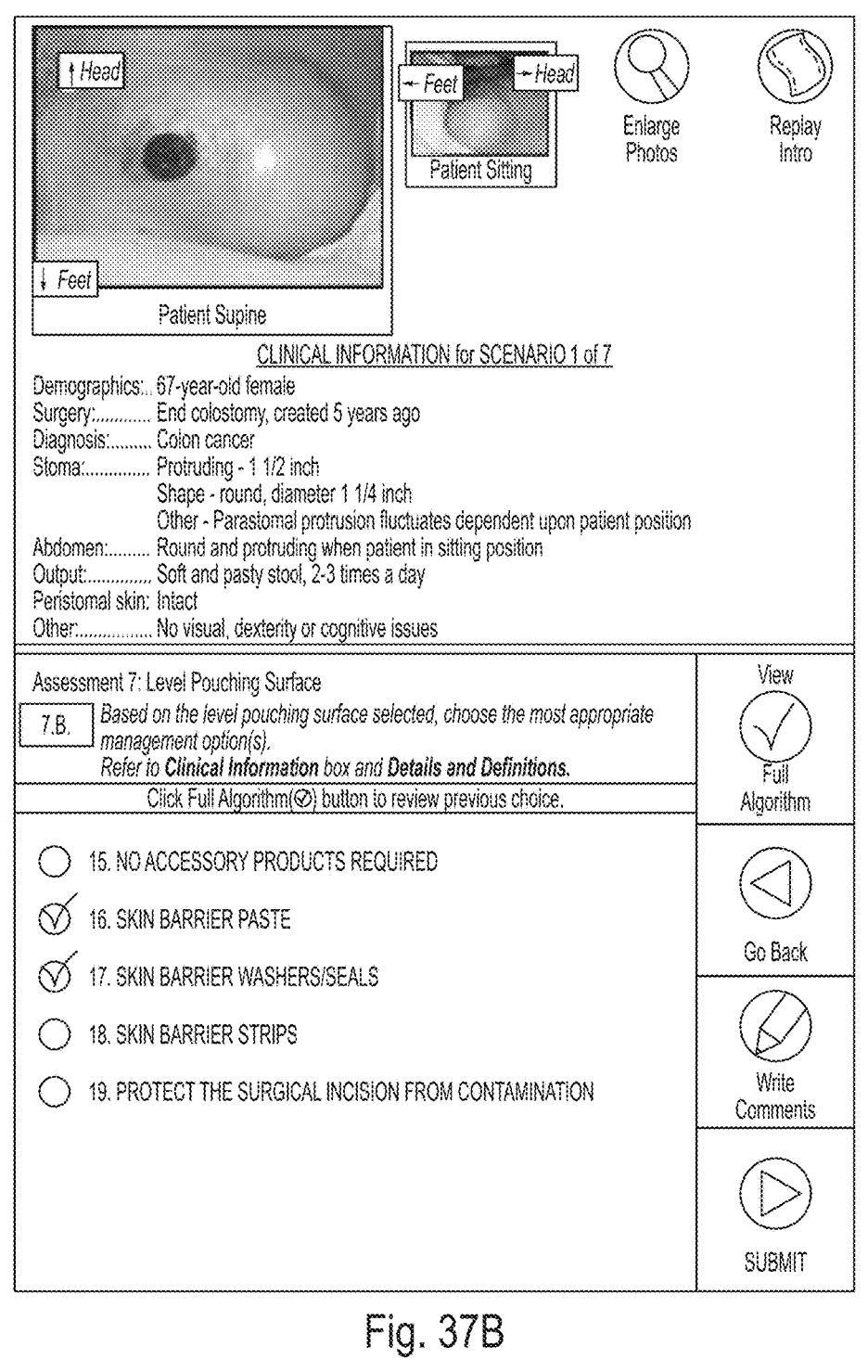

FIGS. 37A and 37B shows a non-limiting example of an interactive tool for construct validation of an ostomy care algorithm using digital real-life clinical scenarios; in this case a tool presenting a GUI for selecting an appropriate management option based on levelness of pouching surface.

FIGS. 38A and 38B shows a non-limiting example of an interactive tool for construct validation of an ostomy care algorithm using digital real-life clinical scenarios; in this case a tool presenting a GUI for selecting ostomy devices, or absence thereof.

FIGS. 39A and 39B shows a non-limiting example of an interactive tool for construct validation of an ostomy care algorithm using digital real-life clinical scenarios; in this case a tool presenting a GUI for selecting stoma complications, or absence thereof.

FIGS. 40A and 40B shows a non-limiting example of an interactive tool for construct validation of an ostomy care algorithm using digital real-life clinical scenarios; in this case a tool presenting a GUI for selecting an appropriate management option based on stoma complications, or absence thereof.

Figure 43B:
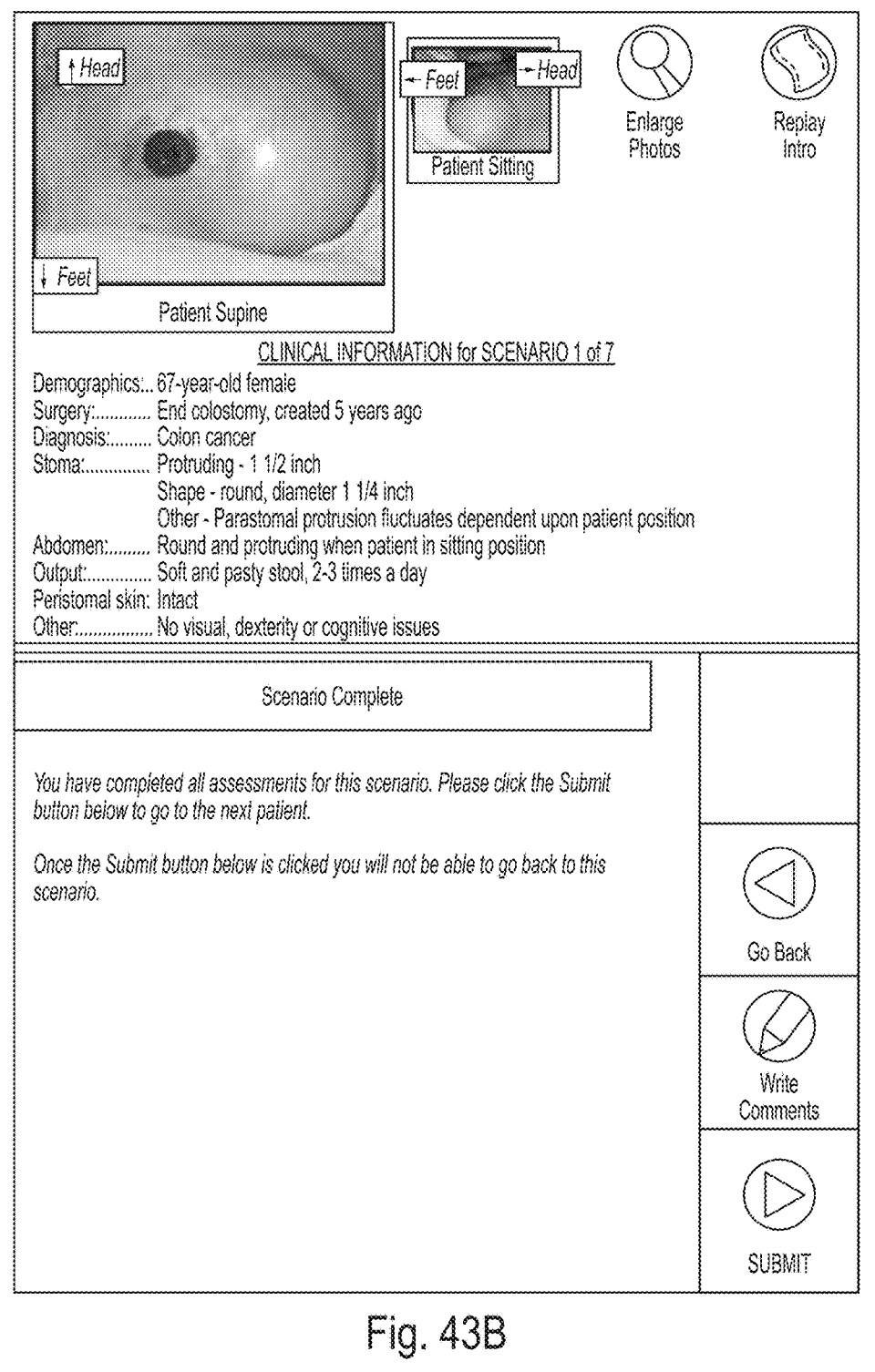

FIGS. 43A and 43B shows a non-limiting example of an interactive tool for construct validation of an ostomy care algorithm using digital real-life clinical scenarios; in this case a tool presenting a GUI for displaying a summary of assessments made and management options selected.

DETAILED DESCRIPTION OF THE INVENTION

Figure 1:
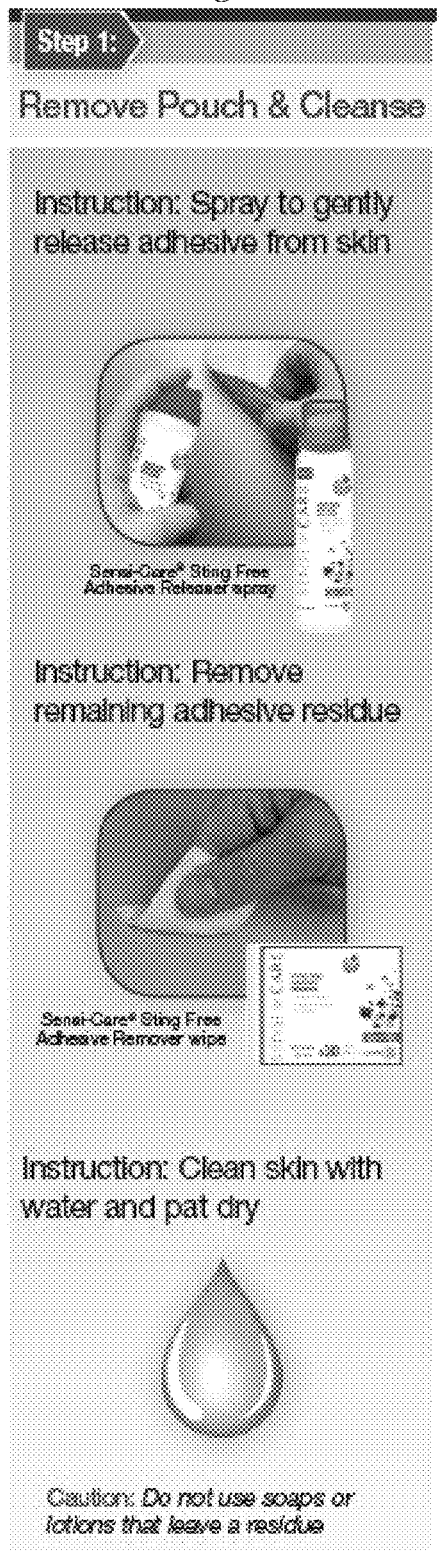
FIG. 1 shows a non-limiting example of a bedside tool for facilitating the methods described herein; in this case, a bedside tool including instructions for removing and cleansing an ostomy pouch.

Current methods of administering ostomy devices and/or products do not employ a full assessment of all the factors necessary to make well informed administration decisions across the full spectrum of healthcare settings including, for example, acute care settings, home health care settings, long-term care settings, and traditional clinical settings. The current methods also fail to adequately standardize decision making through use of a validated algorithm. The technologies currently available fail to provide a convenient, evidence-based instrument that is suitable for use by non-specialized healthcare providers to guide selection of a safe pouching system. Moreover, existing technologies fail to offer access to such a guide in a range of formats such as a bedside tool and an interactive application.

Described herein, in certain embodiments, are methods of administering an ostomy device or product to an individual in need thereof, the method comprising: assessing one or more of: skin adjacent an ostomy, topographical location of any peristomal lesion, stoma type, pouching surface, stoma devices present, and stoma complications to generate ostomy assessment information; applying an algorithm to the ostomy assessment information, the algorithm providing one or more ostomy management options; and administering an ostomy care device or product based on the one or more ostomy management options.

Also described herein, in certain embodiments, are computer-implemented systems comprising: a digital processing device comprising an operating system configured to perform executable instructions and a memory device; and a computer program including instructions executable by the digital processing device to create an interactive ostomy treatment guide comprising: a software module configured to receive ostomy assessment information, the assessment information comprising one or more of: condition of skin adjacent an ostomy, topographical location of any peristomal lesion, stoma type, pouching surface type, stoma devices present, and stoma complications; a software module configured to apply a treatment algorithm to the ostomy assessment information to generate an output; and a software module configured to display one or more ostomy management options based on the output.

Also described herein, in certain embodiments, are non-transitory computer-readable storage media encoded with a computer program including instructions executable by a processor to create an interactive ostomy treatment guide comprising: a software module configured to receive ostomy assessment information, the assessment information comprising one or more of: condition of skin adjacent an ostomy, topographical location of any peristomal lesion, stoma type, pouching surface type, stoma devices present, and stoma complications; a software module configured to apply a treatment algorithm to the ostomy assessment information to generate an output; and a software module configured to display one or more ostomy care management options based on the output.

Also described herein, in certain embodiments, are methods of administering an ostomy device or product to an individual in need thereof, the method comprising: assessing one or more of: skin adjacent an ostomy, topographical location of any peristomal lesion, stoma type, pouching surface, stoma devices present, and stoma complications; applying an algorithm to each assessment, the algorithm providing ostomy care guidance comprising one or more of: at least one ostomy management option, a consideration, at least one device recommendation, at least one product recommendation, an instruction, a treatment, and a caution; and administering an ostomy care device or product to the individual based on each ostomy care guidance.

Also described herein, in certain embodiments, are methods of administering an ostomy care device or product to an individual in need thereof, the method comprising: assessing type of ostomy, type and volume of output, stoma type, stoma profile, stoma shape, abdominal contour, levelness of pouching surface, stoma devices present, stoma complications, peristomal skin condition, and peristomal skin complications; applying an algorithm to each assessment, the algorithm providing ostomy care guidance comprising one or more of: at least one ostomy management option, a consideration, at least one device recommendation, at least one product recommendation, an instruction, a treatment, and a caution; and administering an ostomy care device or product to the individual based on each ostomy care guidance.

Also described herein, in certain embodiments, are computer-implemented systems comprising: a digital processing device comprising an operating system configured to perform executable instructions and a memory device; and a computer program including instructions executable by the digital processing device to create an interactive ostomy treatment guide comprising: a software module configured to receive an assessment of: type of ostomy, type and volume of output, stoma type, stoma profile, stoma shape, abdominal contour, levelness of pouching surface, stoma devices present, stoma complications, peristomal skin condition, and peristomal skin complications; a software module configured to apply a treatment algorithm to each assessment to generate an output; and a software module configured to display one or more ostomy management options based on the output.

Also described herein, in certain embodiments, are non-transitory computer-readable storage media encoded with a computer program including instructions executable by a processor to create an interactive ostomy treatment guide comprising: a software module configured to receive an assessment of: type of ostomy, type and volume of output, stoma type, stoma profile, stoma shape, abdominal contour, levelness of pouching surface, stoma devices present, stoma complications, peristomal skin condition, and peristomal skin complications; a software module configured to apply a treatment algorithm to each assessment to generate an output; and a software module configured to display one or more ostomy management options based on the output.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Interactive Ostomy Treatment Guide

In some embodiments, the methods, systems, and media described herein include an ostomy treatment guide, or use of the same. In further embodiments, an ostomy treatment guide described herein facilitates input and recordation of assessments of various aspects of an ostomy patient. In further embodiments, an ostomy treatment guide described herein facilitates application of an algorithm to provide ostomy management options. Many formats compatible with ease of use, standardization of care, and patient safety are suitable for the guides.

In some embodiments, an ostomy treatment guide described herein comprises an article of manufacture. In further embodiments, an ostomy treatment guide comprises a bedside tool. In still further embodiments, a bedside tool is a durable printed construct adapted for portability and use by a healthcare provider in a clinical setting at the point of patient care.

In some embodiments, an ostomy treatment guide described herein is digital and interactive. For example, in some embodiments, an ostomy treatment guide described herein comprises a computer program. Many types of computer program are suitable. In various embodiments, the computer program is a web application, a mobile application, a standalone application (e.g., executable file, etc.), or a web browser extension or plug-in.

In some embodiments, an ostomy treatment guide described herein facilitates a stepwise assessment of an ostomy. Any number of steps that provides an assessment of the ostomy adequate to make safe management recommendations is suitable. In various embodiments, the ostomy treatment guide facilitates a stepwise assessment of an ostomy comprising about 2, 3, 4, 5, 6, 7, 8, 9, 10, 11, 12, 13, 14, 15, 16, 17, 18, 19, 20, 21, 22, 23, 24, 25, 26, 27, 28, 29, 30 or more steps. In a particular embodiment, the ostomy treatment guide facilitates a 6-step assessment of an ostomy. In another particular embodiment, the ostomy treatment guide facilitates an 11-step assessment of an ostomy.

Figure 4:
FIG. 4 shows a non-limiting example of a bedside tool for facilitating the methods described herein; in this case, a bedside tool including a checklist for assessing stoma type and pouching surface and applying an algorithm to match ostomy management options to the assessment information.
Figure 5:
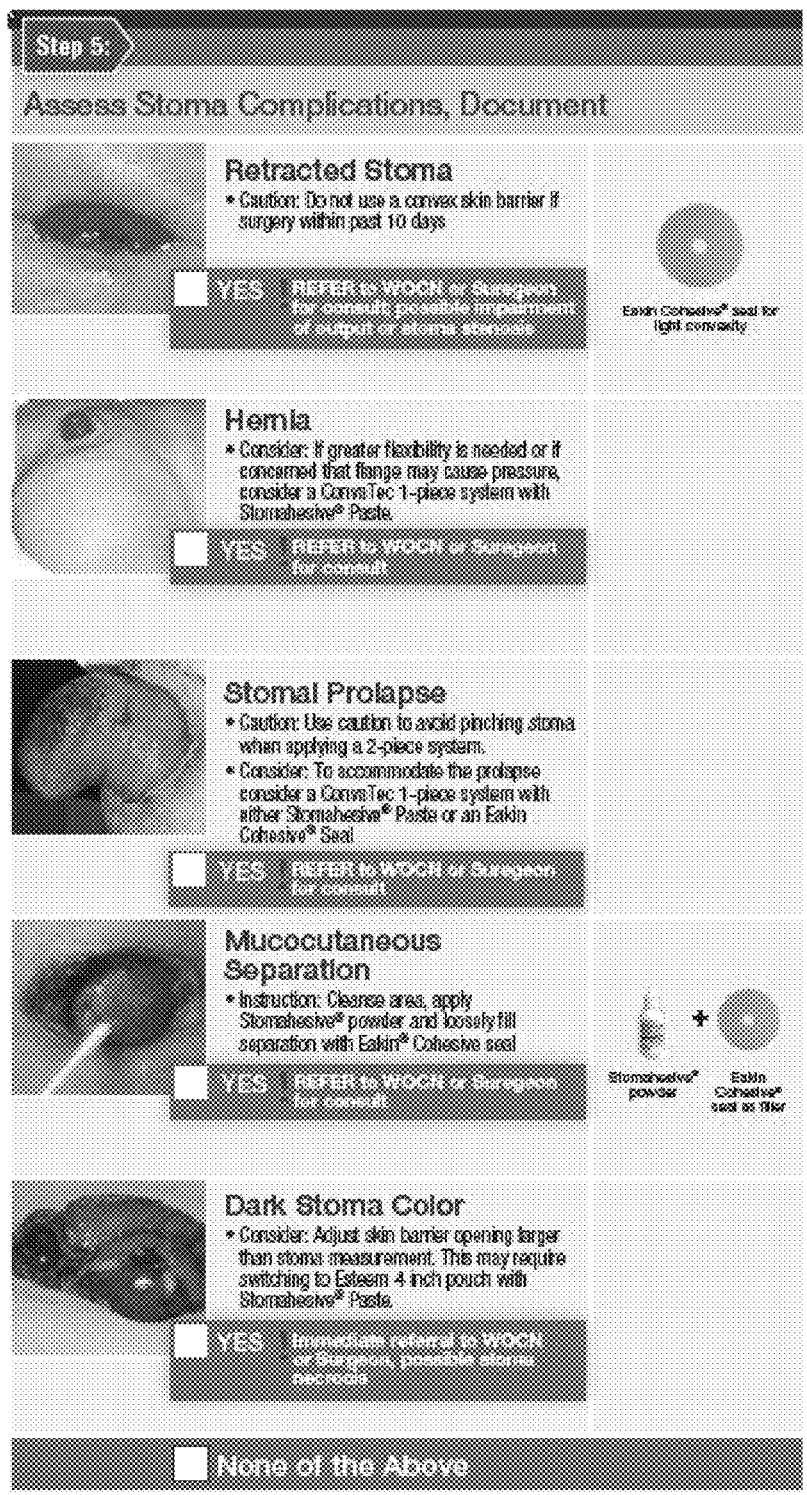
FIG. 5 shows a non-limiting example of a bedside tool for facilitating the methods described herein; in this case, a bedside tool including a checklist for assessing stoma complications and applying an algorithm to match ostomy management options to the assessment information.

In some embodiments, an ostomy treatment guide described herein includes descriptions that facilitate selecting a condition from a list of potential conditions to make an assessment. FIGS. 3-5 show non-limiting, exemplary embodiments of an ostomy treatment guide for use at a patient's bedside. In FIG. 3, peristomal skin assessments are facilitated by text descriptions of 6 potential conditions. In FIG. 4, stoma type, pouching surface, and stoma device assessments are facilitated by text descriptions of potential conditions. In FIG. 5, stoma complication assessments are facilitated by text descriptions of 5 potential conditions. Similarly, FIGS. 10-23 show non-limiting, exemplary embodiments of ostomy treatment algorithms including text descriptions that facilitate selecting a condition from a list of potential conditions to make an assessment. Also, FIGS. 24, 26, 28, 30, 32, and 33 show non-limiting, exemplary embodiments of an interactive tool for construct validation including text descriptions that facilitate selecting a condition from a list of potential conditions to make an assessment.

In some embodiments, an ostomy treatment guide described herein includes images that facilitate selecting a condition from a list of potential conditions to make an assessment. FIGS. 3-5 show non-limiting, exemplary embodiments of an ostomy treatment guide for use at a patient's bedside. In FIG. 3, peristomal skin assessments are facilitated by photographs of 6 potential conditions. In FIG. 4, stoma type, pouching surface, and stoma device assessments are facilitated by photographs of potential conditions. In FIG. 5, stoma complication assessments are facilitated by photographs of 5 potential conditions. Similarly, FIGS. 10-23 show non-limiting, exemplary embodiments of ostomy treatment algorithms including photographs that facilitate selecting a condition from a list of potential conditions to make an assessment. Also, FIGS. 24, 26, 28, 30, 32, and 33 show non-limiting, exemplary embodiments of an interactive tool for construct validation including photographs that facilitate selecting a condition from a list of potential conditions to make an assessment.

Figure 2:
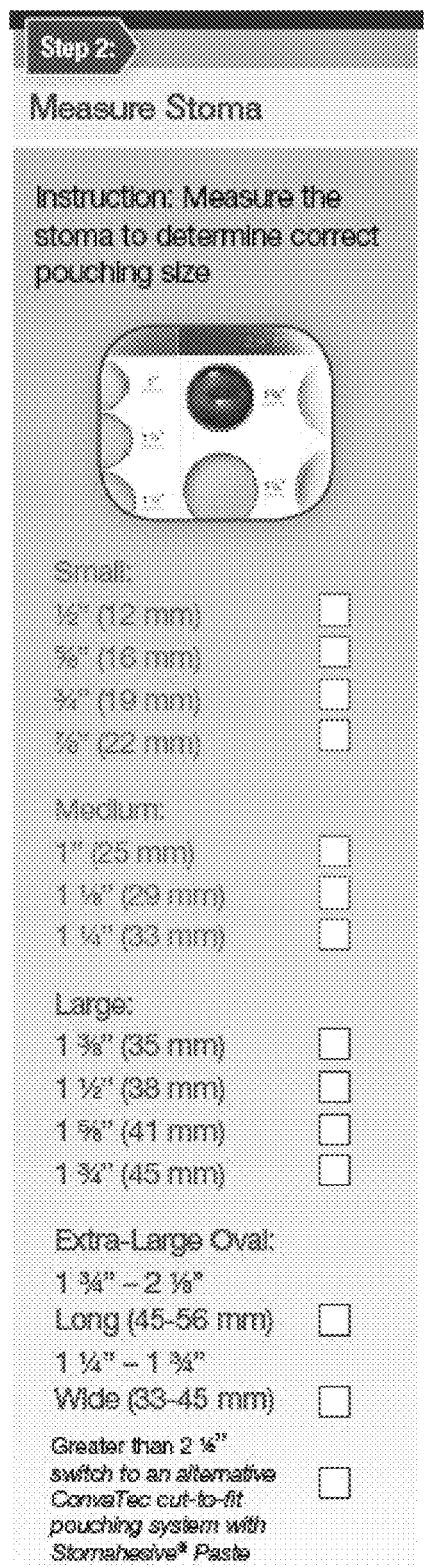
FIG. 2 shows a non-limiting example of a bedside tool for facilitating the methods described herein; in this case, a bedside tool including instructions for measuring and classifying an ostomy stoma based on size and shape.
Figure 6:
FIG. 6 shows a non-limiting example of a bedside tool for facilitating the methods described herein; in this case, a bedside tool including instructions for applying an ostomy system.
Figure 7:
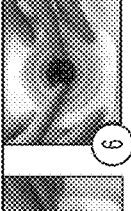
FIG. 7 shows a non-limiting example of a bedside tool for facilitating the methods described herein; in this case, a bedside tool including ostomy system application tips.
Figure 9:
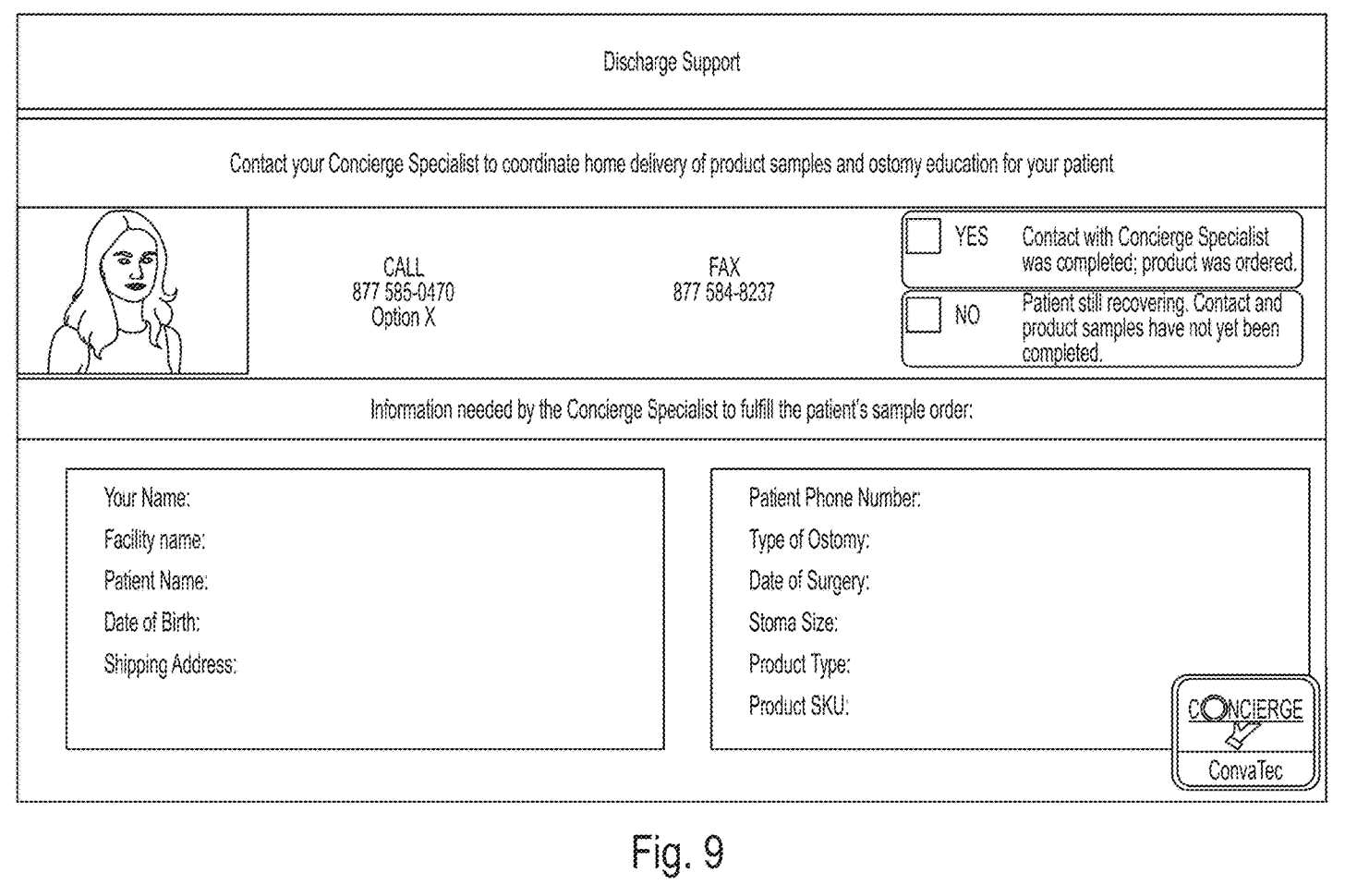
Figure 11:
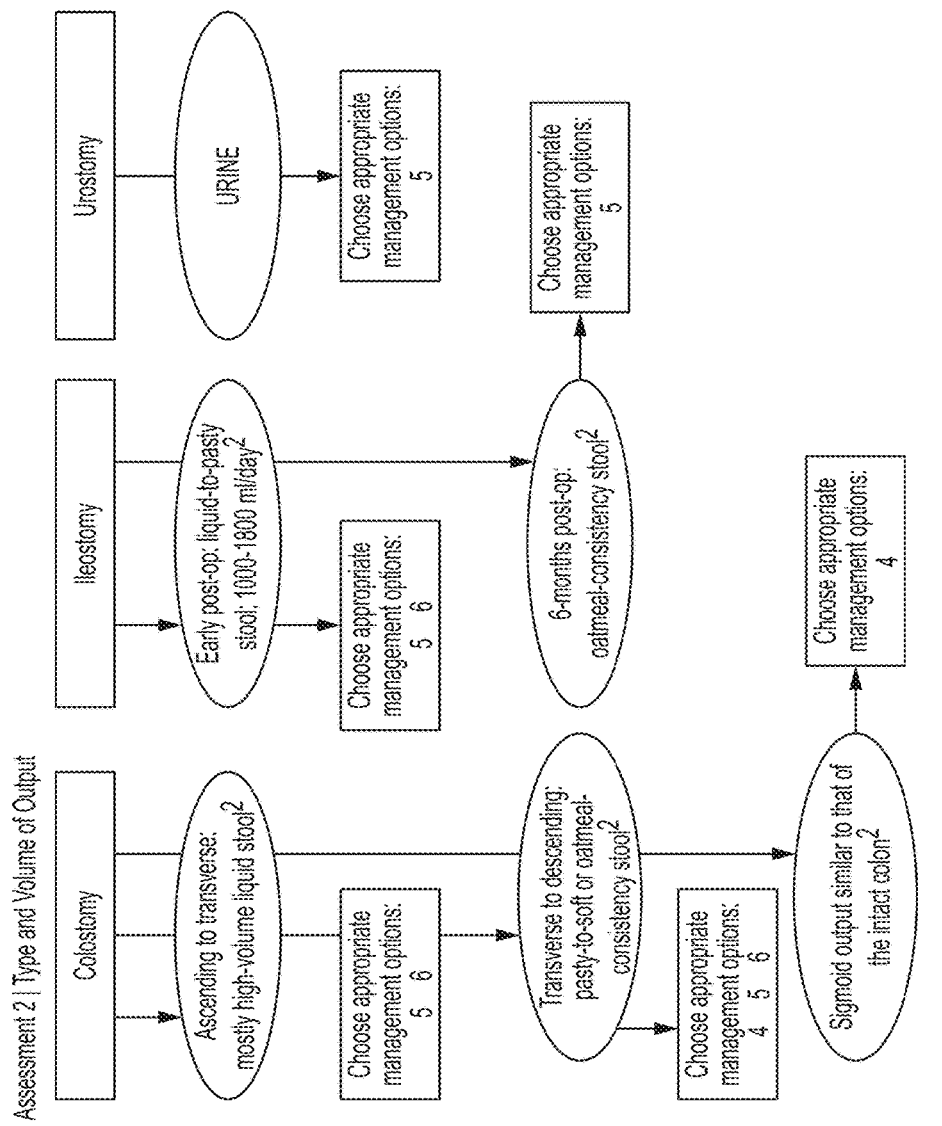
FIG. 11 shows a non-limiting example of an ostomy treatment algorithm; in this case, an algorithm matching assessments pertaining to type and volume of output with ostomy management options.
Figure 13:
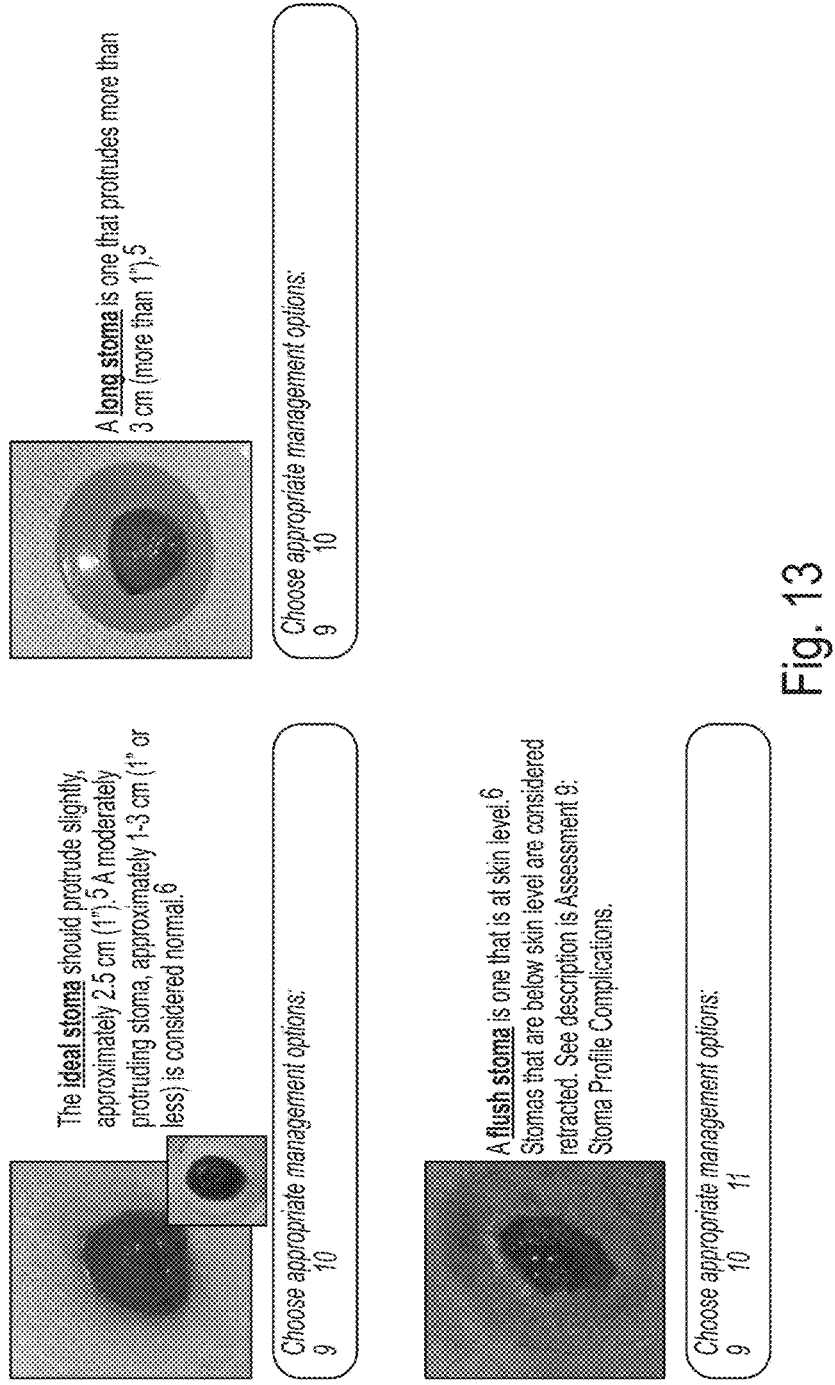
FIG. 13 shows a non-limiting example of an ostomy treatment algorithm; in this case, an algorithm matching assessments pertaining to stoma profile with ostomy management options.
Figure 14:
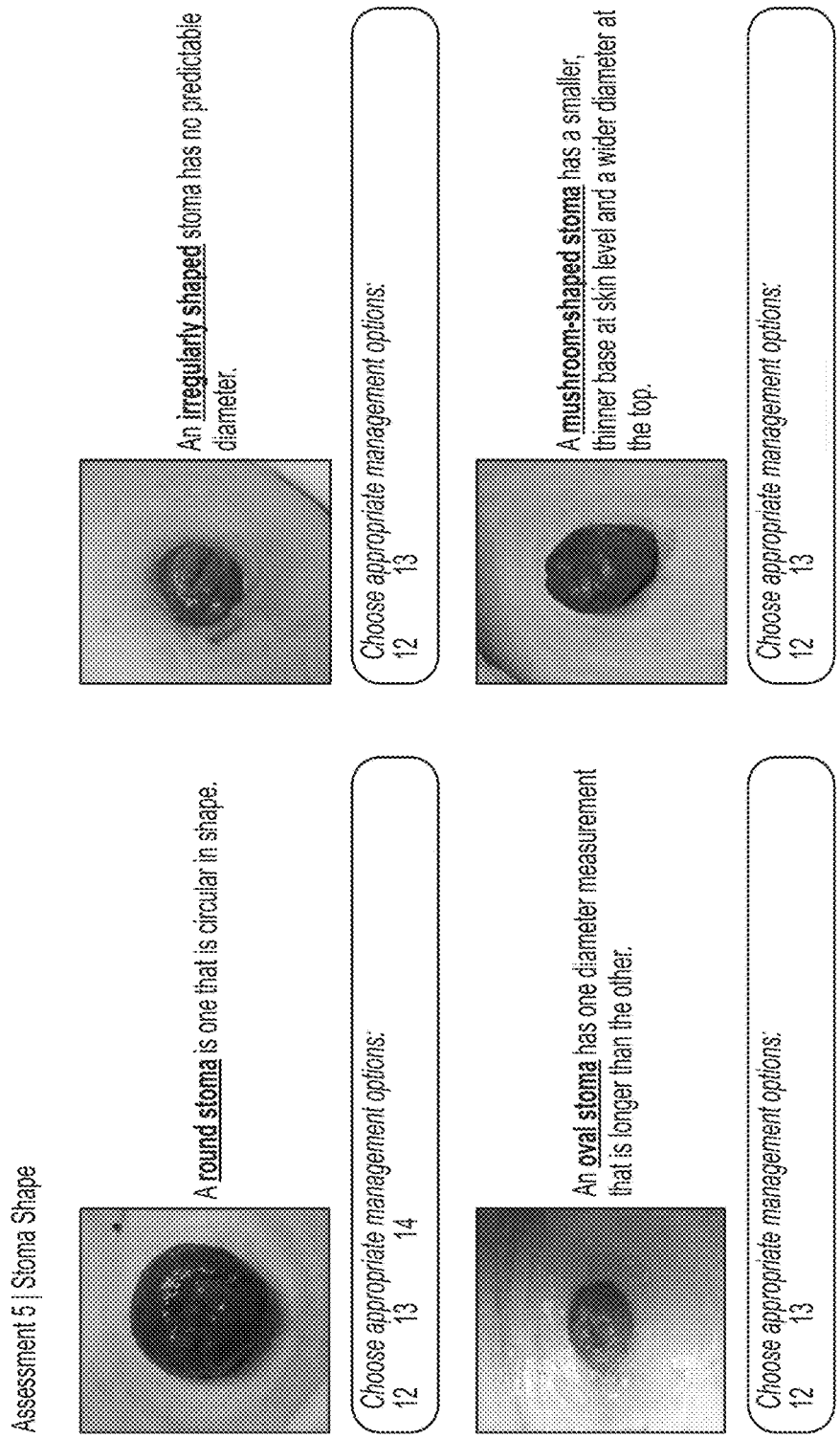
FIG. 14 shows a non-limiting example of an ostomy treatment algorithm; in this case, an algorithm matching assessments pertaining to stoma shape with ostomy management options.
Figure 20:
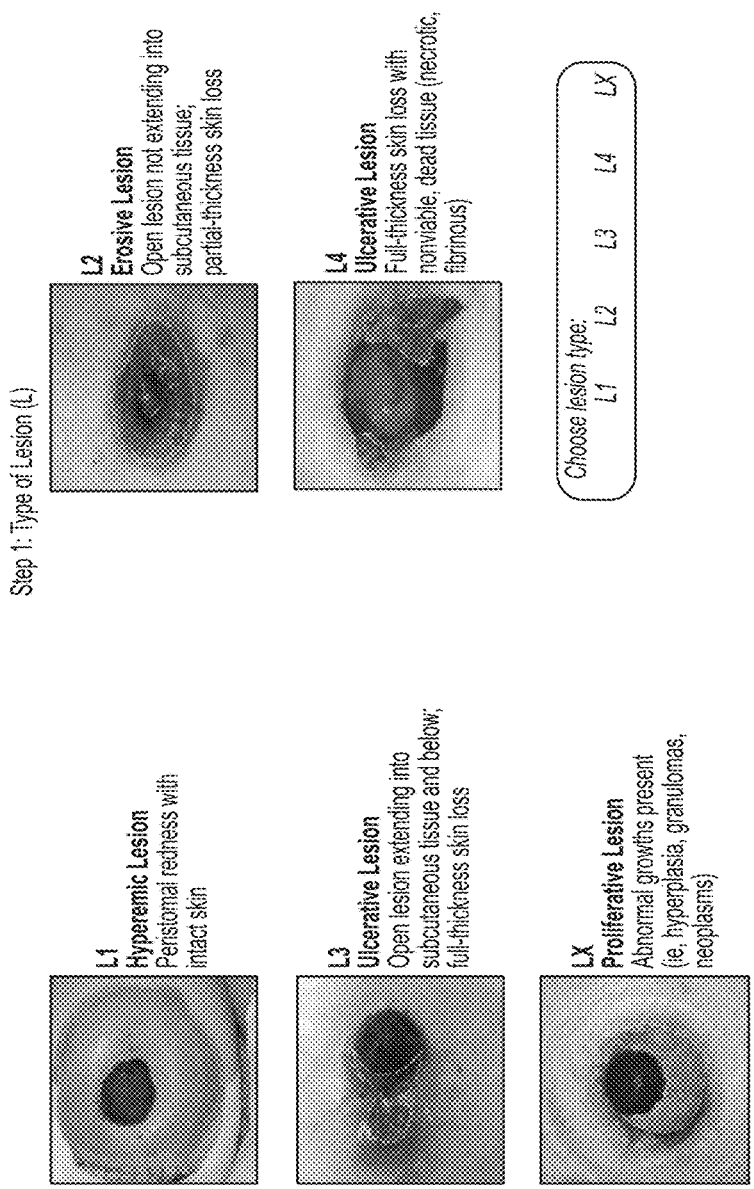
FIGS. 20-21 show non-limiting examples of an ostomy treatment algorithm; in this case, an algorithm matching assessments pertaining to peristomal skin assessment with ostomy management options.
Figure 21:
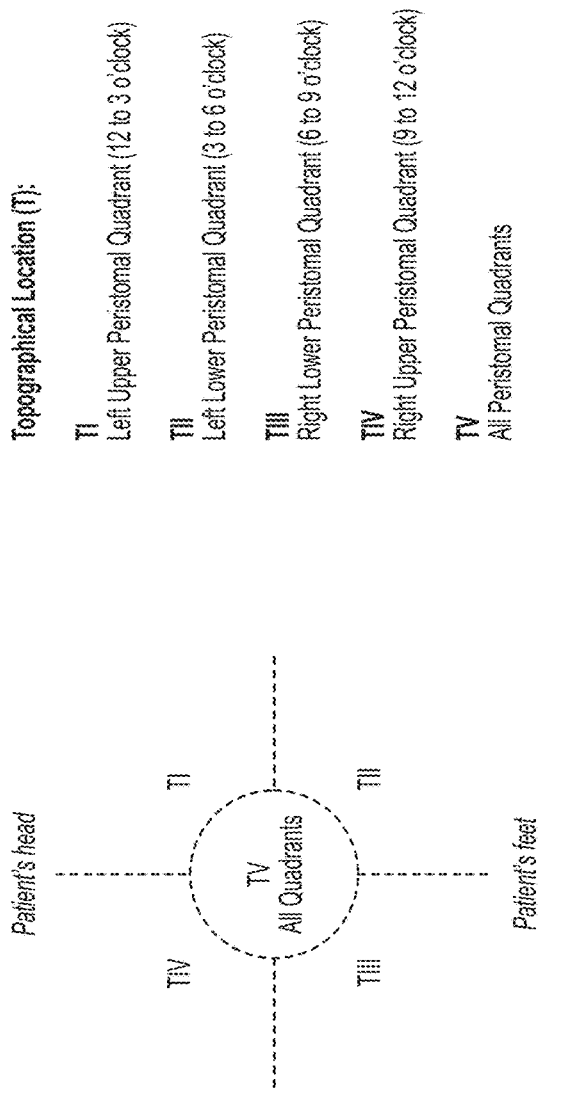
Figure 22:
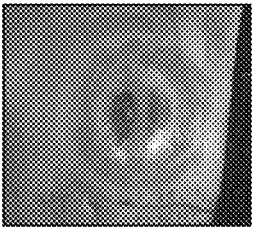
Figure 24A:
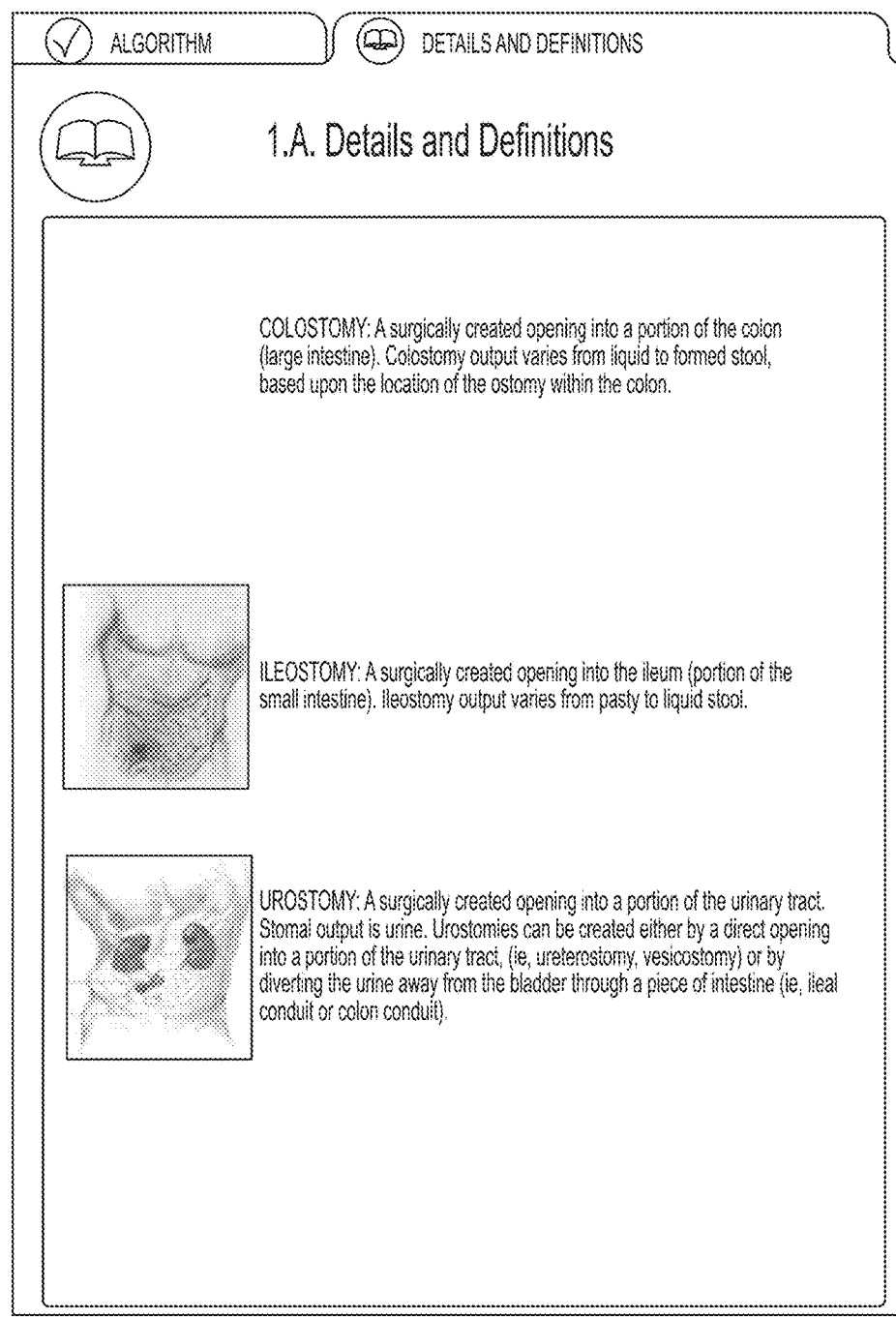
Figure 25B:
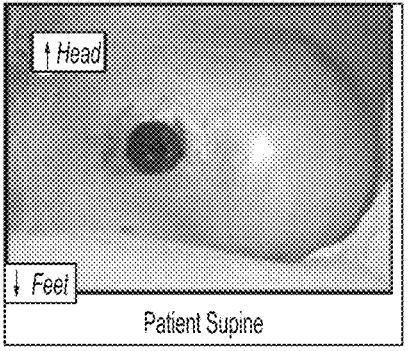
Figure 26A:
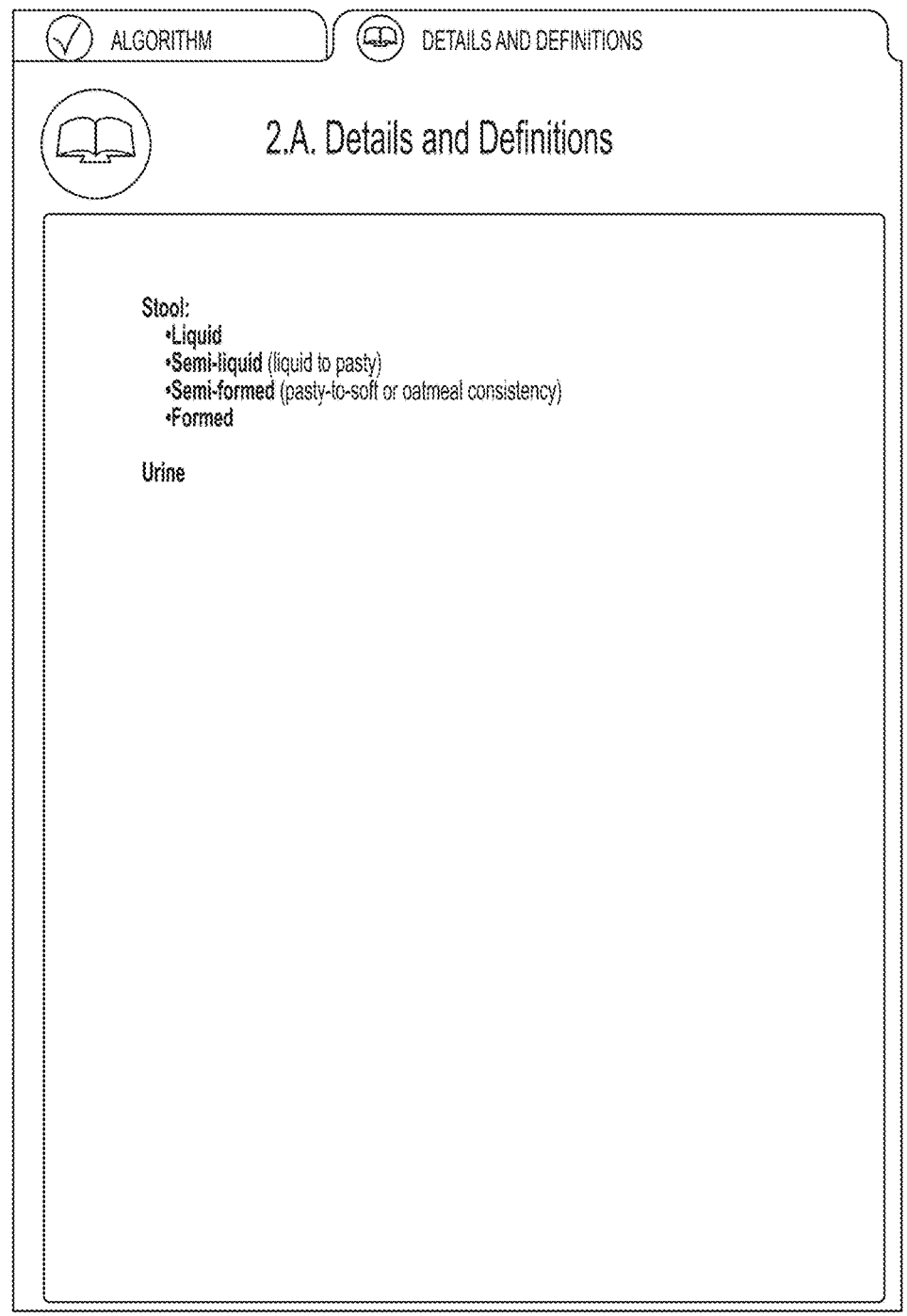
Figure 27A:
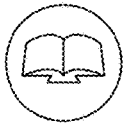
FIGS. 27A and 27B shows a non-limiting example of an interactive tool for construct validation of an ostomy care algorithm using digital real-life clinical scenarios; in this case a tool presenting a GUI for selecting an appropriate management option based on type and volume of output.
Figure 27B:
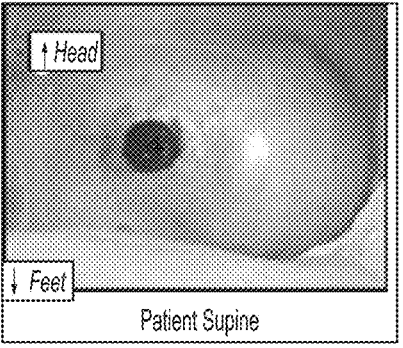
Figure 30A:
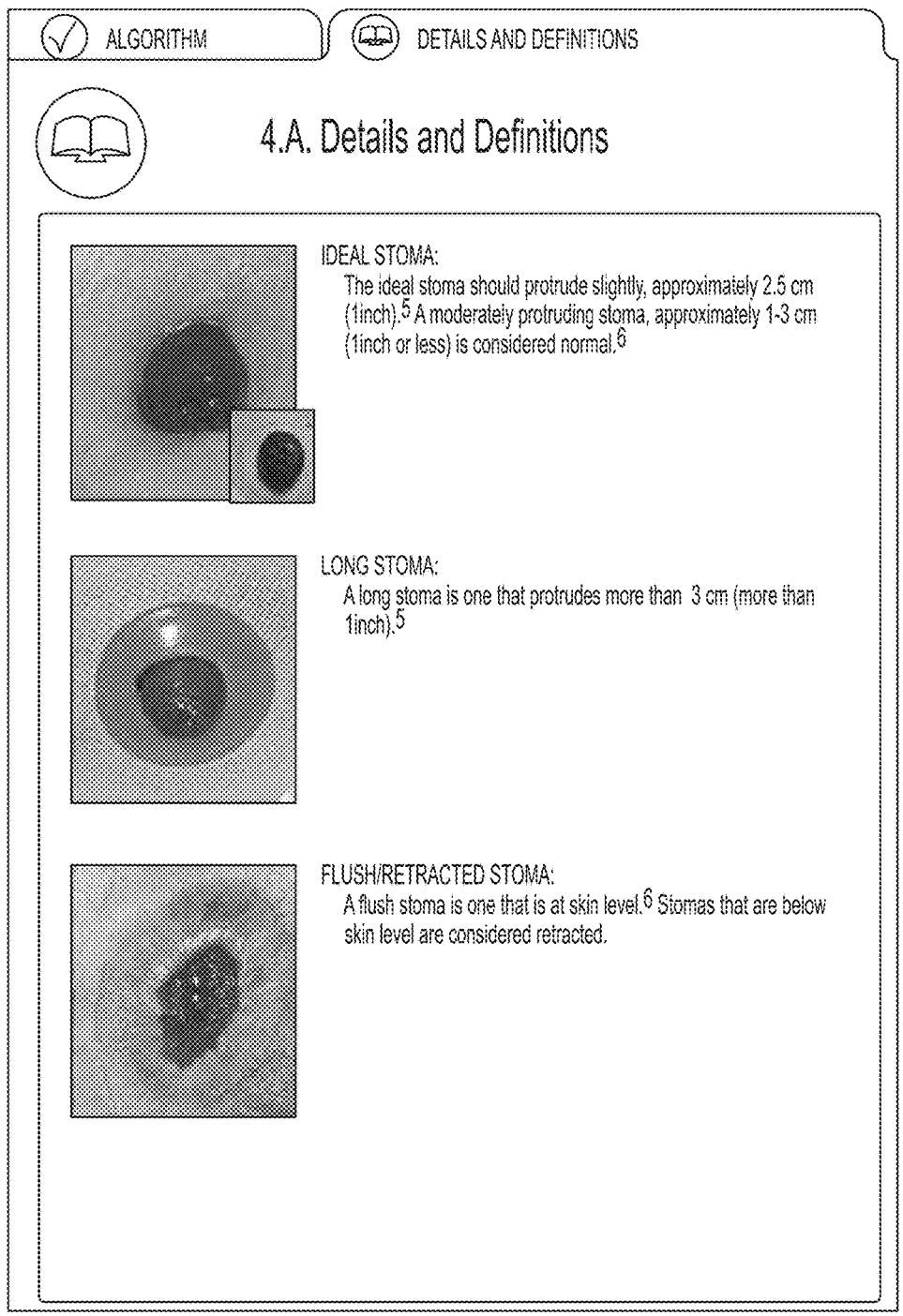
Figure 31B:
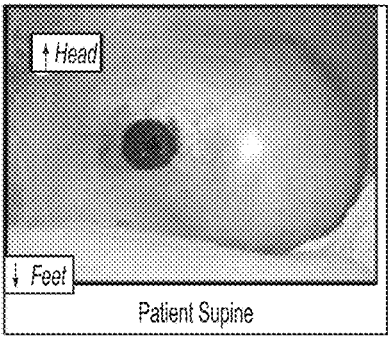
Figure 32A:
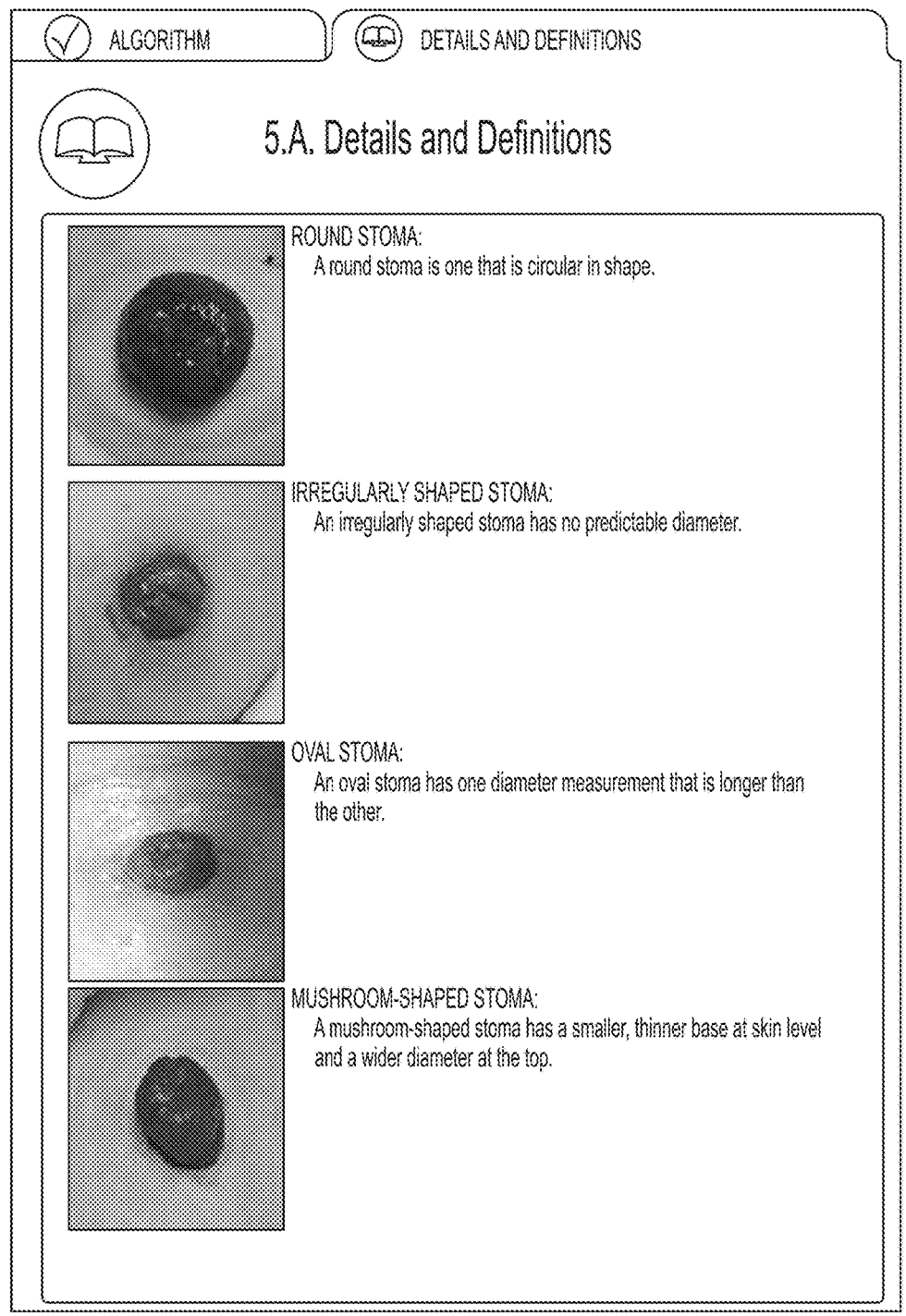
Figure 33B:
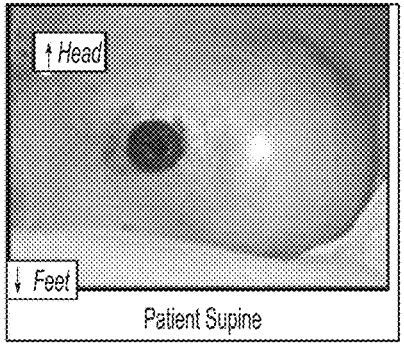
Figure 35B:
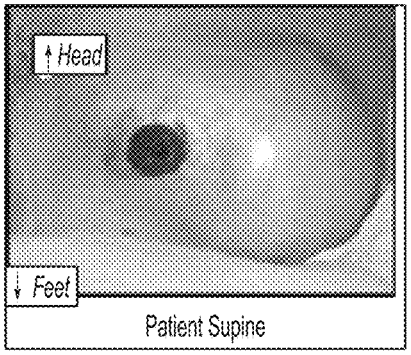
Figure 36A:
FIGS. 36A and 36B shows a non-limiting example of an interactive tool for construct validation of an ostomy care algorithm using digital real-life clinical scenarios; in this case a tool presenting a GUI for selecting levelness of pouching surface.
Figure 36B:
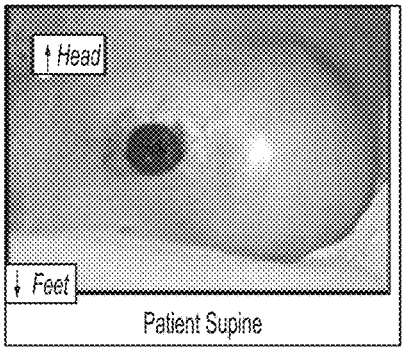
Figure 38B:
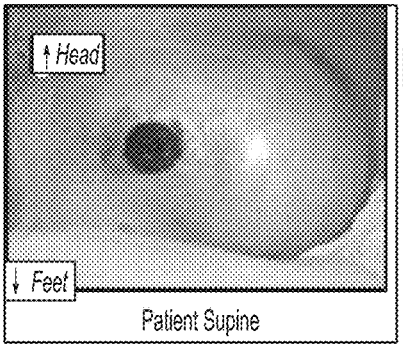
Figure 39B:
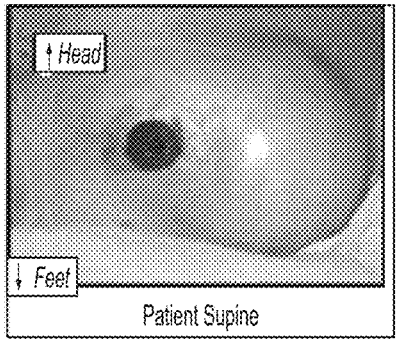
Figure 40B:
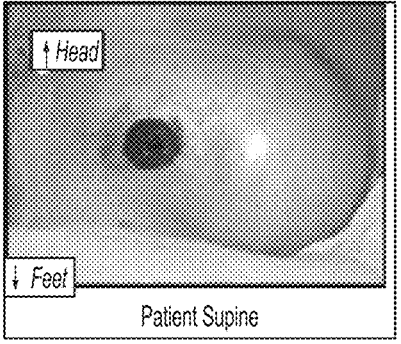
Figure 41A:
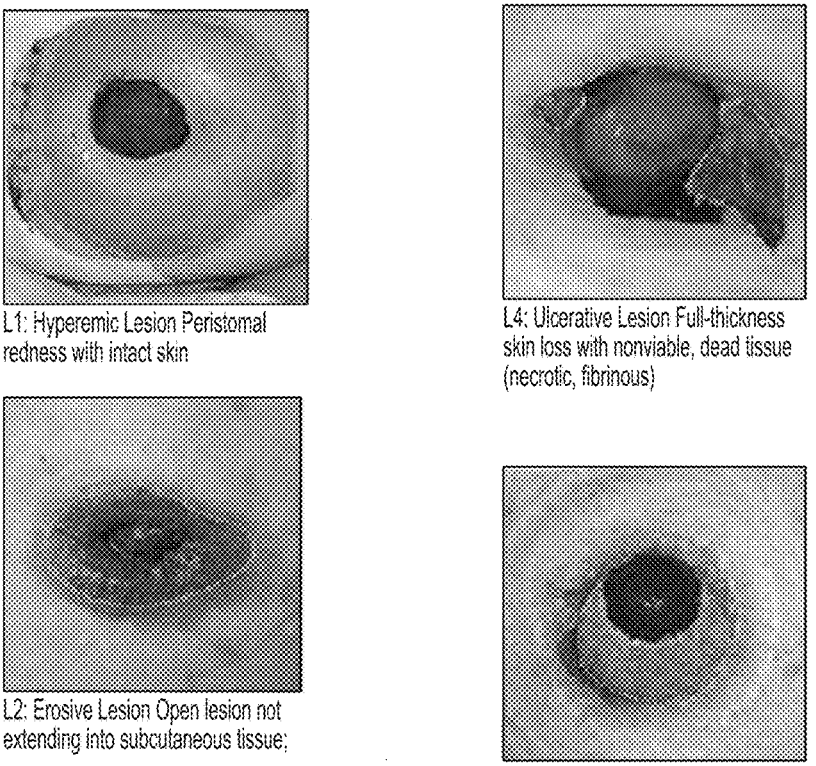
FIGS. 41A and 41B shows a non-limiting example of an interactive tool for construct validation of an ostomy care algorithm using digital real-life clinical scenarios; in this case a tool presenting a GUI for selecting peristomal skin condition (e.g., presence or absence of lesions).
Figure 41B:
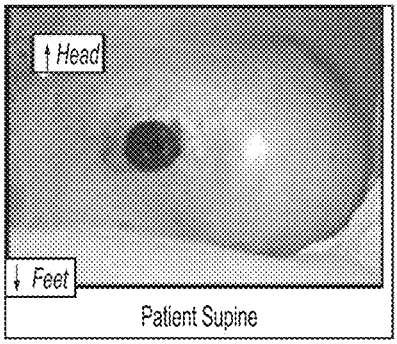
Figure 42A:
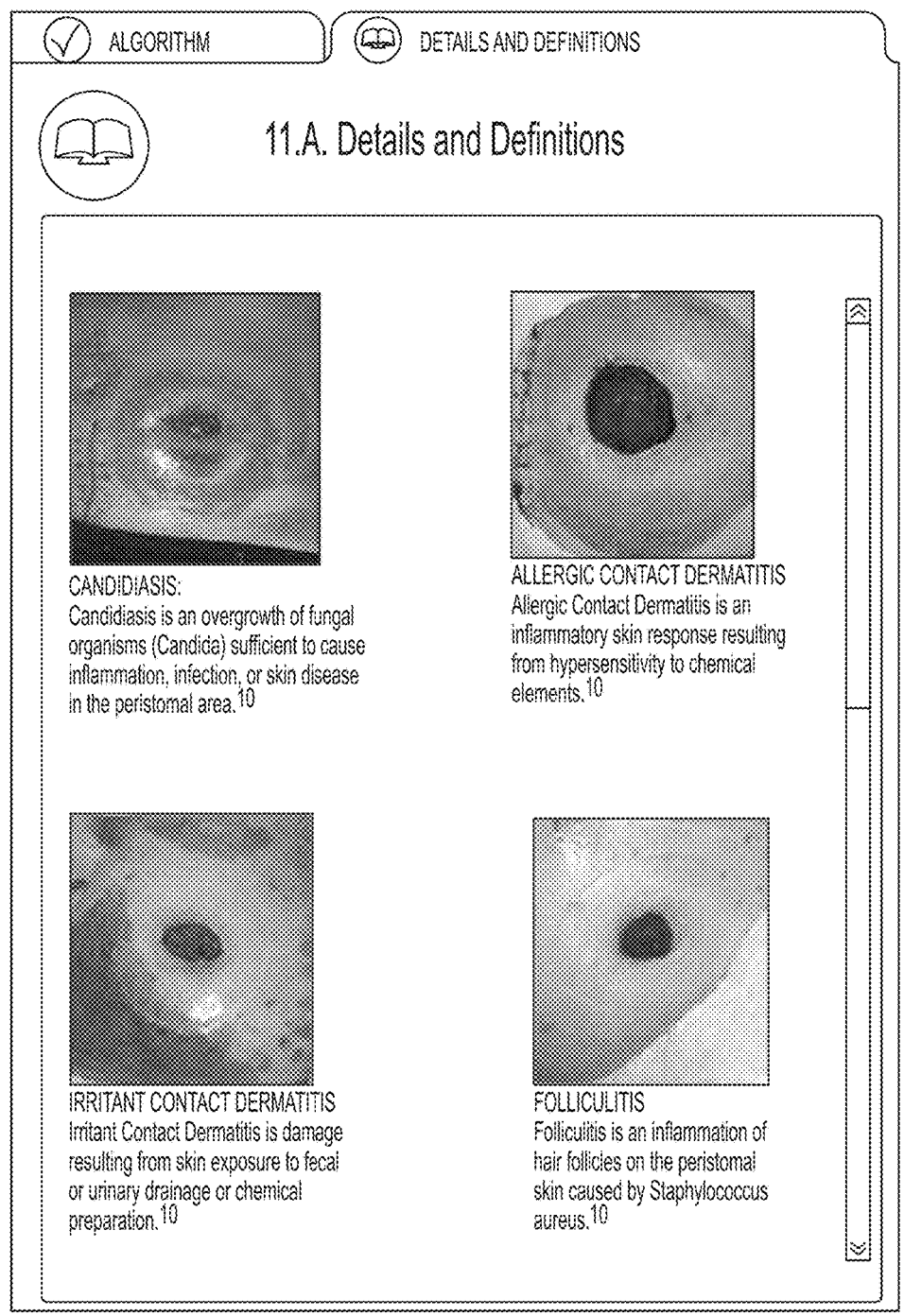
FIGS. 42A and 42B shows a non-limiting example of an interactive tool for construct validation of an ostomy care algorithm using digital real-life clinical scenarios; in this case a tool presenting a GUI for selecting peristomal skin complications, or absence thereof.
Figure 42B:
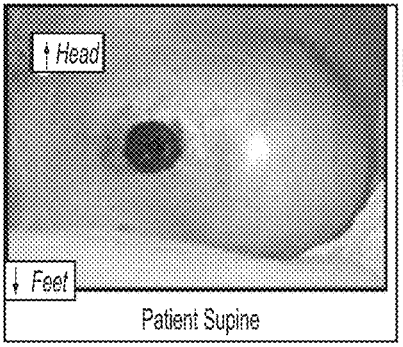

In some embodiments, an ostomy treatment guide described herein includes further information useful in the clinic with regard to providing care to a patient with an ostomy. By way of example, in a particular embodiment, an ostomy treatment guide for use at a patient's bedside includes instructions for removing and cleansing an ostomy pouch. See FIG. 1. By way of further example, in a particular embodiment, an ostomy treatment guide for use at a patient's bedside includes instructions for measuring an ostomy stoma. See FIG. 2. By way of further example, in a particular embodiment, an ostomy treatment guide for use at a patient's bedside includes instructions for applying an ostomy system. See FIG. 6. By way of further example, in a particular embodiment, an ostomy treatment guide for use at a patient's bedside includes ostomy system application tips. See FIG. 7. By way of further example, in a particular embodiment, an ostomy treatment guide for use at a patient's bedside includes troubleshooting information for common ostomy issues. See FIG. 8. By way of yet further example, in a particular embodiment, an ostomy treatment guide for use at a patient's bedside includes information for using and contacting a discharge support service. See FIG. 9.

In some embodiments, an ostomy treatment guide described herein is made available in a language other than English in order to facilitate use by non-English speaking healthcare providers. In further embodiments, an ostomy treatment guide is available in one or more languages including, by way of non-limiting examples, English, Spanish, Italian, Portuguese, French, Dutch, Polish, German, Russian, Ukrainian, Mandarin, Wu, Cantonese, Hindi, Punjabi, Bengali, Marathi, Urdu, Arabic, Turkish, Tamil, Farsi, Japanese, Korean, Vietnamese, Thai, Burmese, Malay, Telugu, Javanese, and Tagalog.

Ostomy Assessments

In some embodiments, the methods, systems, and media described herein include one or more ostomy assessments. In further embodiments, an ostomy assessment is made by a healthcare provider (e.g., a physician, a surgeon, a nurse practitioner, a physician's assistant, a specialized nurse, a registered nurse, a home health nurse, a certified vocational nurse, and the like). In some embodiments, an ostomy assessment generates ostomy assessment information, to which an algorithm is applied in order to provide ostomy management options.

Many ostomy assessments are suitable to generate inputs for an algorithm providing ostomy management options. In some embodiments, an ostomy assessment is, for example, a measurement made by a healthcare provider (e.g., measurement of an ostomy stoma, etc.). In some embodiments, an ostomy assessment is, for example, a quantitative observation by a healthcare provider (e.g., volume of ostomy output, etc.). In some embodiments, an ostomy assessment is, for example, a qualitative observation by a healthcare provider (e.g., stoma shape, abdominal contour, etc.). In some embodiments, an ostomy assessment is, for example, a diagnostic test performed by a healthcare provider. In some embodiments, an ostomy assessment is, for example, a patient question or survey delivered by a healthcare provider.

In some embodiments, an ostomy assessment is made by selecting a condition reflective of the patient's current condition from a list of potential conditions. In further various embodiments, an assessment is made of, by way of examples, skin adjacent an ostomy, topographical location of any peristomal lesion, stoma type, pouching surface, stoma devices present, stoma complications, and the like. In further various embodiments, an assessment is made of, by way of examples, type of ostomy, type and volume of output, stoma type, stoma profile, stoma shape, abdominal contour, levelness of pouching surface, stoma devices present, stoma complications, peristomal skin condition, location of stoma, peristomal skin complications, and the like.

Ostomy Treatment Algorithm

In some embodiments, the methods, systems, and media described herein include an ostomy treatment algorithm, or use of the same. In further embodiments, an algorithm provides one or more ostomy management options by matching ostomy assessment information to at least one ostomy care product or device. In some embodiments, an algorithm is a standalone, single-step algorithm and provides one or more ostomy management options based on a single assessment. In other embodiments, an algorithm is multi-step algorithm and provides one or more ostomy management options based on a plurality of assessments. In further various embodiments, an algorithm is multi-step algorithm and provides one or more ostomy management options based on about 2, 3, 4, 5, 6, 7, 8, 9, 10, 11, 12, 13, 14, 15, 16, 17, 18, 19, 20, 21, 22, 23, 24, 25, 26, 27, 28, 29, 30 or more assessments.

FIGS. 10-23 demonstrate an 11-step ostomy treatment algorithm. By way of example, FIG. 10 demonstrates the first step of an ostomy treatment algorithm, wherein ostomy assessment information pertaining to type of ostomy is matched to ostomy management options. Continuing to refer to FIG. 10, an assessment indicting colostomy is matched to management options 1 and 2; an assessment indicting ileostomy is matched to management option 1; and an assessment indicting urostomy is matched to management option 3.

Ostomy Management Options

In some embodiments, the methods, systems, and media described herein include one or more ostomy management options, or use of the same. In some embodiments, an ostomy treatment algorithm is applied to ostomy assessment information to generate one or more ostomy management options. In some embodiments, one ostomy management option is provided based on ostomy assessment information. In other embodiments, a plurality of ostomy management options are provided based on ostomy assessment information. In various further embodiments, about 2, 3, 4, 5, 6, 7, 8, 9, 10, 11, 12, 13, 14, 15, 16, 17, 18, 19, 20, 21, 22, 23, 24, 25, or more ostomy management options are provided. In some embodiments, ostomy management options are provided by an option number which is subsequently used to reference a management option key or library.

Many types of ostomy management options are suitable. In some embodiments, ostomy management options include one or more ostomy care device recommendations or one or more ostomy care product recommendations. In some embodiments, ostomy management options include a negative recommendation for one or more ostomy care devices or products (e.g., a non-recommendation, device or product to be avoided, etc.). By way of example, referring to FIG. 4, ostomy management options based on an assessment of pouching surface indicating a soft & flaccid abdomen, include a product recommendation (e.g., ConvaTec Belt). In some embodiments, ostomy management options include one or more ostomy care instructions. In some embodiments, ostomy management options include one or more ostomy care treatments. In some embodiments, ostomy management options include one or more ostomy care considerations. In some embodiments, ostomy management options include one or more ostomy care cautions. By way of example, referring to FIG. 3, ostomy management options based on an assessment of proliferative lesion on peristomal skin, include a caution (e.g., refer to expert for treatment). By way of further example, referring to FIG. 5, ostomy management options based on an assessment of stoma complications, include a caution (e.g., refer to WOCN).

Tables 1-10 demonstrate examples of ostomy management options associated with a particular ostomy assessment.

TABLE 1

| Assessment 1: Type of Ostomy | 1. DRAINABLE POUCH: A pouch with an opening at the bottom that is wide enough to empty solid stool. These pouches have two options for tail closures. 1) A detachable tail clamp is separate from the pouch. The patient should have enough hand strength to securely close the clamp. 2) An integrated tail closure for patients who prefer this option or if they have dexterity issues. Recommended for solid to |

TABLE 1-continued semi-solid stool, or liquid stool that has a lot of particulate matter. Not recommended for purely liquid stool or urine.
2. CLOSED END POUCH: A pouch without an opening or clamp at the bottom (also known as a non-drainable pouch). Recommended for solid to semi-solid stool. Not recommended for liquid stool or urine.
3. UROSTOMY POUCH: A pouch with a spout (tap/spigot) at the bottom to drain output. Recommended for urine or liquid stool with very little particulate matter. Not recommended for solid stool or liquid stool that has a lot of particulate matter.

TABLE 2

| | |
|---|---|
| Assessment 2: Type and Volume of Output | 4. REGULAR-WEAR SKIN BARRIERS: have a solid-formed adhesive material that protects the skin from stoma effluent. Recommended for solid and semi-solid stool, humid climates or patients who perspire a lot. Not recommended for liquid stool or urine.<br>5. EXTENDED-WEAR SKIN BARRIERS: have a solid-formed adhesive material with delayed absorption and higher level of adhesion, and will protect the skin from stoma output. Recommended for extra resistance against erosion of skin barrier in the presence of liquid to semi-liquid stool and urine. Generally provide a longer wear time than regular wear skin barriers. Not recommended for patients who frequently change their skin barrier, live in a humid climate or patients who perspire a lot.<br>6. HIGH VOLUME OUTPUT POUCH: A pouch holding a higher volume of output than other pouches, with a spout (tap/spigot) at the bottom to drain output. Recommended for ileostomates with high-volume liquid stool with very little particulate matter. Not recommended for solid or semisolid stool or for liquid stool that has a lot of particulates. |

TABLE 3

| | |
|---|---|
| Assessment 3: Type of Stoma | 7. SPECIAL CONSIDERATIONS FOR A LOOP OSTOMY SUPPORT DEVICE: If a loop ostomy support device is in place, the skin barrier should accommodate the device. If loop ostomy rod support is not sutured to skin, the skin barrier may be gently slid underneath the rod. Caution should be exercised at all times to avoid dislodging loop ostomy support device (i.e.: loop ostomy rod, red rubber catheter).<br>8. SPECIAL CONSIDERATIONS FOR A DOUBLE BARREL STOMA: When a double barrel stoma is created, the functioning end is called the proximal stoma and the non-functioning end is called the distal stoma or mucus fistula. The mucous fistula may temporarily drain fecal output and/or mucous. Ideally, the separation between stomas will be approximately 3". Both stomas may be pouched independently. Optionally, both stomas maybe included in one pouch if the skin barrier surface will accommodate them. |

TABLE 4

| | |
|---|---|
| Assessment 4: Stoma Profile | 9. ONE-PIECE POUCHING SYSTEM: In one-piece pouching systems, the skin barrier and pouch are attached together. Recommended for ease of application-particularly for patients with poor vision or dexterity, post-operatively and when there is need for a more flexible skin barrier than a two-piece system. It may have a lower profile. Not recommended for patients who want to switch between different pouches (e.g., drainable and closed-end), or for whom easy stoma access is necessary.<br>10. TWO-PIECE POUCHING SYSTEM: In two-piece pouching systems with flanges, the skin barrier and pouch are separate, but each has a semi-rigid or adhesive ring to attach the two parts. Recommended for patients with no vision or dexterity issues, for patients who want to switch between different pouches (e.g., drainable and closed-end) or post-operatively (when an adaptor is used to reduce pressure on abdomen or the two pieces are connected before applying). Not recommended when there is a need for a more flexible skin barrier.<br>11. CONVEX POUCHING SYSTEM: A skin barrier that is curved toward the abdomen to push inward around the stoma and peristomal skin, making the stoma protrude further. Recommended for use with flush or retracted stomas, flaccid abdomens, and when peristomal creases, skin folds or wrinkles are present. Not recommended for use with a protruding stoma or firm flat abdomen. Monitor closely to ensure pressure ulcerations do not develop. |

TABLE 5

| | |
|---|---|
| Assessment 5: Stoma Shape | 12. MOLDABLE SKIN BARRIER: A barrier that adheres to the skin and has a starter hole that is molded using the thumbs and fingers to match the size and shape of the stoma. The molding action creates a roll of adhesive that will hug the wall of the stoma so that the skin is not exposed. No cutting or pattern making is necessary with this barrier. Paste and washers are not generally needed with moldable barriers. Recommended for all stoma types, immediately after surgery and beyond, per the patient's preference. Also recommended for patients with visual, dexterity or cognitive issues or allergies to paste or other accessories. Not recommended for patients with a stoma size greater than 2⅛ inch.<br>13. CUT-TO-FIT SKIN BARRIER: A barrier that adheres to the skin and has a small starter hole that the user will cut to a larger opening to match the shape of the stoma. Usually, a pattern mirroring the stoma shape is made and then the skin barrier is cut with rounded scissors to match the pattern, allowing for minimal peristomal skin exposure. Jagged cutting edges should be smoothed to avoid lacerations of the stoma. Paste or accessories products should be used to eliminate any exposed skin around the stoma. Recommended for all stoma shapes, immediately after surgery or beyond, per the patient's preference. Not recommended for patients with visual, dexterity or cognitive issues. |

TABLE 5-continued

14. PRE-CUT SKIN BARRIER: A barrier that adheres to the skin and has a stoma opening already cut to a specific stoma diameter. Minimal or no cutting is needed. These barriers should closely match the stoma size and shape, allowing for minimal peristomal skin exposure to stool or urine. Paste or accessories products should be used to eliminate any exposed skin around the stoma. Recommended for round stomas at least 6 weeks post surgery when stoma has reduced to its permanent shape. Recommended for use with paste, seals or other accessory products. Not recommended for irregular stoma shapes, for fresh postoperative stomas, or for the first 6 weeks following surgery as stoma will shrink.

TABLE 6

| | |
|---|---|
| Assessment 6: Abdominal Contour | Selections should be the same as for Assessment 4. See Table 4. |

TABLE 7

| | |
|---|---|
| Assessment 7: Level Pouching System | 15. NO ACCESSORY PRODUCTS REQUIRED<br>16. SKIN BARRIER PASTE: is used to fill in uneven areas. It is placed as caulking around the cut edge of the solid skin barrier to prevent an undermining of the seal by stool or urine between the skin barrier and the peristomal skin. Recommended for use with cut-to-fit or pre-cut skin barriers to protect peristomal skin. Not recommended for patients with allergies/sensitivities or directly on broken peristomal skin.<br>17. SKIN BARRIER WASHERS/SEALS: are constructed of solid skin barrier material, and have no laminating film on top. These can be molded into various shapes to mirror the image of the pouching surface, and can also add mild convexity to a pouching system. They can be applied directly to the skin or added to the skin barrier. Recommended for use with cut-to-fit or pre-cut skin barriers to protect peristomal skin or when mild convexity is desired. Not recommended for patients with allergies/sensitivities.<br>18. SKIN BARRIER STRIPS: are constructed of solid skin barrier material in various lengths and thicknesses. They are used to fill an uneven area and provide an additional skin barrier around the stoma. Recommended for use when creases or folds in the pouching surface must be addressed to create a level pouching surface. Not recommended for patients with allergies/sensitivities.<br>19. PROTECT THE SURGICAL INCISION FROM CONTAMINATION: by stool or urine by removing the pouching system in a direction away from the incision. Assure a secure skin barrier seal at all times to help prevent leakage of effluent on the incision area. |

TABLE 8

| | |
|---|---|
| Assessment 8: Presence/Absence of Devices | 20. SPECIAL CONSIDERATIONS FOR A LOOP OSTOMY SUPPORT DEVICE: (same as option 7) If a loop ostomy support device is in place, the skin barrier should accommodate the device. If loop ostomy rod support is not sutured to skin, the skin barrier may be gently slid underneath the rod. Caution should be exercised at all times to avoid dislodging loop ostomy support device (i.e.: loop ostomy rod, red rubber catheter).<br>21. EXERCISE CAUTION SO AS NOT TO DISLODGE URETERAL STENTS: during pouch change. Stents should be threaded into the pouch without tension. Exercise caution when applying pouch to flange to avoid pinching stents or the stoma at connection point. |

TABLE 9

| | |
|---|---|
| Assessment 9: Presence/Absence of Stoma Complications | 22. MODIFY OPENING OF SKIN BARRIER: As the stoma changes with hernia size, re-measure skin barrier size and shape; choose larger pouching system size as needed.<br>23. INCREASE FLEXIBILITY: CONSIDERATION: If the patient is wearing a two-piece pouching system, a one-piece pouching system may provide more flexibility and a more secure seal between the skin barrier and the skin.<br>24. TWO-PIECE POUCHING SYSTEM: (same as option 10) In two-piece pouching systems with flanges, the skin barrier and pouch are separate, but each has a semi-rigid or adhesive ring to attach the two parts. Recommended for patients with no vision or dexterity issues, for patients who want to switch between different pouches (e.g., drainable and closed-end) or post-operatively (when an adaptor is used to reduce pressure on abdomen or the two pieces are connected before |

TABLE 9-continued applying). Not recommended when there is a need for a more flexible skin barrier.
25. SUPPORT BELTS: are available in several widths, based upon the patient's abdominal musculature and size of hernia. They are made from an elastic material that provides support for the hernia, and have a reinforced opening that allows the pouch to be unrestricted. A hernia support belt should be applied when the patient is lying down. Consult with a WOC Nurse, ostomy supplier or manufacturer for ordering information.
26. HERNIA SUPPORT BELT WITH PROLAPSE FLAP: As above (option 25), this belt has an additional elastic flap that is secured over the pouch in an attempt to prevent a prolapsed from further enlarging. Consult with a WOC Nurse, ostomy supplier or manufacturer for ordering information
27. USE CONVEXITY WITH CAUTION. The inappropriate use of convexity may place undue pressure on peristomal tissues. Close patient monitoring needs to occur to avoid adverse events (such as pressure ulcers) from the use of convexity.
28. SKIN BARRIER FILMS/WIPES: provide skin protection from stripping during adhesive removal. They are applied by gently wiping around the peristomal area prior to application of the skin barrier. Recommended for use on intact peristomal skin only. Not recommended for use directly on broken skin or on people who have a history of skin sensitivities. NOTE: An adhesive remover wipe should be used when removing/changing the skin barrier.
29. AVOID SHEAR TO SKIN: Adhesive tape removal can cause shear and skin stripping. Most ostomy pouching systems have tape collars on the skin barrier. There is no need to add additional adhesive tape. All tape should be removed with caution to avoid skin damage.
30. POUCH SUPPORT BELT: Some pouches are manufactured with belt tabs on each side where a thin elastic belt can be attached. Recommended to provide extra support to the pouch during patient movement.
31. REFERRAL TO A WOC NURSE: Consider referring patient to a Wound Ostomy and Continence (WOC) Nurse for assistance with management. If not available locally, contact manufacturers for additional assistance.
32. REFERRAL TO SURGEON: Consider referring patient to surgeon and/or physician (when indicated).
33. STOOL SOFTENERS: For patients with fecal stomas, stool softeners or laxatives may be needed for stool to pass through narrowed opening.
34. FREQUENT STOMA OBSERVATION: When the stoma needs frequent observation, transparent pouches allow for easier visualization.
35. RESIZE SKIN BARRIER: (same as option 22) A necrotic stoma undergoes an evolution where part of the mucosa begins to turn pale, and then grayish and black from lack of an adequate blood supply. This tissue will eventually slough off and a foul odor is noted. The skin barrier may need to be resized as necrotic tissue sloughs as the stoma size and/or shape may change.
36. CLEANSE AFFECTED AREA: When a wound is noted at the juncture of the mucous membrane of the stoma and the skin, it is called a Mucocutaneous Separation. Stool and debris need to be cleaned off of the area with saline or water.
37. TREAT THE WOUND: In order to help create a level pouching surface, and treat the wound of a Mucocutaneous Separation, loosely fill separated area with absorbent product (paste, powder, or wound dressing such as Hydrofiber); Secure with a thin adherent wound dressing such as a thin hydrocolloid then pouch over the area.

TABLE 10

| | |
|---|---|
| Assessment 11: Presence/Absence of Peristomal Skin Complications | 38. ANTIFUNGAL POWDER: If limited to peristomal area, lightly sprinkle with topical antifungal powder (do not use antifungal cream that would interfere with pouch seal) and "crust" area with either a skin protectant wipe without alcohol or a moistened finger.<br>39. POUCH CHANGE FREQUENCY: Consider increasing frequency of pouch changes.<br>40. REFERRAL TO A WOC NURSE: (same as option 31) Consider referring patient to a Wound Ostomy and Continence (WOC) Nurse for assistance with management. If not available locally, contact manufacturers for additional assistance.<br>41. REFERRAL TO SURGEON: (same as option 32) Consider referring patient to surgeon and/or physician (when indicated)<br>42. PERISTOMAL SHAVING: Shave in the direction that the hair grows. It is recommended an electric razor be used. If a safety razor is used, apply a mild soap or shaving cream. The skin should be washed, rinsed and dried thoroughly prior to applying a new pouching system.<br>43. REMOVE THE IRRITANT<br>44. RESIZE SKIN BARRIER: (same as option 22): Adjust skin barrier opening to fit snugly around the stoma to eliminate chronic exposure to output and moisture.<br>45. LIMIT NUMBER OF PRODUCTS IN CONTACT WITH SKIN (i.e., accessory products).<br>46. EXTENDED-WEAR SKIN BARRIERS: (same as option 5) have a solid-formed adhesive material with delayed absorption and higher level of adhesion, and will protect the skin from stoma output. Generally provide a longer wear time than |

TABLE 10-continued regular wear skin barriers. Recommended for extra resistance against erosion of skin barrier in the presence of liquid to semi-liquid stool and urine. Not recommended for patients who frequently change their skin barrier, live in a humid climate or patients who perspire a lot.

47. INCREASE FLUID INTAKE: For urinary diversions, have patient increase fluid intake to help keep urine acidic.

48. SKIN CLEANSING: Gentle technique for cleansing and/or pouching system removal. Avoid the use of soaps with lotions as they will interfere with the ability of the skin barrier to adhere to the skin.

49. SKIN BARRIER FILMS/WIPES: provide skin protection from stripping during adhesive removal. They are applied by gently wiping around the peristomal area prior to application of the skin barrier. Recommended for use on intact peristomal skin only. Not recommended for use directly on broken skin or on people who have a history of skin sensitivities. NOTE: An adhesive remover wipe should be used when removing/changing the skin barrier.

50. SKIN PROTECTANT POWDER: A hydrocolloid based powder that absorbs moisture to create a dry surface for the skin barrier to adhere to. Apply by lightly dusting on moist or denuded skin, brush off excess and dab with a skin barrier film/wipe or a moistened finger to form a "crust." Recommended for use on moist, weepy or denuded skin. Not recommended for use on dry intact skin or for patients with known sensitivities/allergies to the product.

51. PAIN MANAGEMENT AS DIRECTED

52. TOPICAL TREATMENT AS DIRECTED

Digital Processing Device

In some embodiments, the methods, systems, and media described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-Transitory Computer Readable Storage Medium

In some embodiments, the methods, systems, and media disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the methods, systems, and media disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Software Modules

In some embodiments, the methods, systems, and media disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the methods, systems, and media disclosed herein include one or more databases, or use of the same. In view of the disclosure provided herein, those of skill in the art will recognize that many databases are suitable for storage and retrieval of ostomy patient, ostomy assessment, ostomy management option, ostomy device, and ostomy product information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, and methods described herein and are not meant to be limiting in any way.

Example 1—Validation of an Interactive Algorithm for Ostomy Care

Abstract

Purpose: A study was conducted to obtain construct validation data for a previously face and content validated Ostomy Algorithm using digital real-life clinical scenarios.

Design: A cross-sectional, mixed methods web-based survey design study was conducted.

Subjects and Setting: A total of 297 English speaking Registered Nurses completed the study. They included both expert and non-expert RNs. Participants represented both acute and post acute settings, with one expert ostomy nurse (WOC Nurse) to two non expert nurses.

Methods: Following written consent, respondents answered demographic questions, and completed a brief algorithm tutorial. Then seven ostomy-related clinical scenarios consisting of real-life photos and pertinent clinical information were presented to study participants electronically. See FIGS. 24-34. Respondents used the 11 assessment components of the digital algorithm to choose management options. Participant written comments about the scenarios and the research process were collected.

Results: The mean overall percentage of correct responses was 84.23%. Mean percentage of correct responses for respondents with a self-reported basic ostomy knowledge was 87.7%; for those with a self-reported intermediate ostomy knowledge was 85.88% and those who were self reported experts in ostomy care achieved 82.77% correct response rate. Five respondents reported having no prior ostomy care knowledge at screening and achieved an overall 45.71% correct response rate. No negative comments regarding the algorithm were recorded by participants.

Conclusion: The new standardized Ostomy Algorithm remains the only face, content and construct validated digital clinical decision instrument currently available world-wide. Further research on application at the bedside while tracking patient outcomes is warranted.

Development of a New Ostomy Algorithm

The Ostomy Algorithm was developed to help healthcare providers at both the expert and non-expert level support patient safety by facilitating optimum ostomy product selection upon completion of eleven assessments. An electronic content validity study of the algorithm with one hundred sixty six ostomy care experts resulted in a strong overall Content Validity Index (CVI) of 0.95 of a potential 1.0. Each assessment score obtained a CVI of 0.90 to 0.98.

Construct Validation Study

Research Objectives

The purpose of this study was to obtain construct validation data for the Ostomy Algorithm using digital real-life clinical scenarios. Construct validation will answer the following research question: Does use of the Ostomy Algorithm guide the clinician to a safe product choice for a particular patient?

Methods

Study Design

A cross sectional, mixed-methods, web-based, survey study design was chosen. The study design was developed by the sponsor's WOC nurses and refined with expert working group input. The study plan was finalized to include seven scenarios with real-time photography and accompanying clinical text. The seven scenarios represented ostomy assessments that nurses commonly encounter in clinical practice.

Sample Inclusion/Exclusion Criteria

English speaking and reading registered nurses who were currently in practice and caring for a minimum of one ostomy patient per month met inclusion criteria. When respondents accessed the site by invitation, they were asked to complete eleven screening questions that determined their eligibility to participate. When screening criteria were successfully met, participants were asked to provide electronic consent to continue. If they chose to decline, a "thank you" screen appeared, and they were not granted access to the study screens. As respondents met inclusion criteria, study access was provided on a first-come, first-serve basis until the pre-established sample requirements had been met.

Sample Size

A representative quota sample of 300 US based nurses was established as the recruitment goal. Recruitment goal was 100 expert ostomy care nurses and 200 registered nurses with little or no expertise in ostomy care. Subjects were recruited from both acute and post-acute care settings.

Instruments

The Ostomy Algorithm was used for this study as it currently remains the only face and content validated published instrument that assists healthcare providers with selection of safe products and management strategies.

Study Development

Photographs and clinical information for the scenarios were obtained from current sponsor WOC nurse consultants. Each of the seven scenarios was reviewed and revised by the representative expert working group over the course of fifteen months, at which time face validation was completed. Over 120 photos were reviewed for consideration of inclusion within the seven clinical scenarios. Once final draft was developed, text and photos were reviewed and revised by the representative working group a minimum of 9 times until the final product was approved.

The sponsor entered into a partnership with two third-party vendors to develop the electronic construct validation platform and manage study data. See FIGS. 24-34. Companies were chosen based upon expertise in developing electronic studies and integrity of data management. Clinical scenarios were provided to the first vendor for conversion to a digital format. The entire development and editing process took twelve months, during which the project team members and the representative expert working group provided input for revising study screens and addressing questions.

Answer keys for each scenario and overall scoring criteria were developed by the project team and distributed to the representative expert working group for comment and verification of correctness. See Example 2. When finalized, these documents were provided to both vendors. The second vendor, a market research and analytic company with a dedicated life sciences focus managed the study logistics, data management and scoring per the established criteria.

Participants were randomly recruited by the vendor electronically from two US-based registered nurse source lists. A list of nurses registered within the sponsor's database and an additional nurse contact list purchased by the vendor were used. The population for recruitment totaled over 100,000 nurses; approximately 22,000 from the sponsor database and 788,000 from the vendor database. Over 31,000 total invitations were sent. The study was conducted over a seven-week period.

Data Analysis

Sample, demographics, and all raw data were collected and housed by the third party vendor utilizing a technology platform of end-to-end quantitative market research. When the study was complete, a final report was delivered to the sponsor in the Microsoft Excel 7 (Redmond, Wash.) format. Study results were reviewed by the project team and analyzed by the authors. Any data outliers or areas in question were addressed by the vendor. Additional analyses were requested by the project team utilizing SAS version 9.2. (Cary, N.C.), to compare results among various demographic groups. Raw data and summary data tables were provided to the authors.

Results/Discussion

Participants

A total of 1,439 nurses responded to the study invitation prior to study closure. Decision to close the study was made when targeted quotas were met. Seventy-seven percent (229) of participants were recruited from the list of nurses obtained by the vendor and twenty-three percent (68) were recruited from the sponsor list. Of the 1,439 respondents, 1,005 did not qualify to participate either due to failure of one or more inclusion criteria during initial screening, or segment quotas had been met. One hundred thirty seven (137) nurses who qualified began the study and did not complete all seven scenarios. A total of 297 nurses met inclusion criteria and completed the study.

Demographics

Geographically, participants represented 41 states. Four of the top five states are located within the east coast and California, likely related to overall population. A majority, (86.5%) of participants was female, and ranged in age from 36 years to 65 years (85%). Seven participants (2%) received their basic nursing education outside of the United States; six participants did not have English as their primary language. All were currently licensed and practicing. Study participants represented both acute and post-acute healthcare settings. Of the 182 respondents whose primary practice setting was in acute care, a majority (41.2%) of facilities represented were large facilities, containing 300 or more patient care beds. Twenty two and one half percent of respondents worked in facilities with 200-299 beds, 21.4% worked at facilities with 100-199 beds and 14.8% worked in small facilities with less than 100 beds.

Participant Expertise in Ostomy Care

No identifiable trends among practice setting, state of practice, and level of expertise caring for patients with an ostomy were noted. All study participants, both in acute and postacute settings, were asked if they had access to a WOC Nurse or Ostomy Specialist. One hundred eighty nine participants responded to the question, and approximately two-thirds (60.3%) confirmed they had access to a WOC Nurse and one-third (39.7%) did not. Almost one-half of study participants (46.8%) treated one to five ostomy patients per month. Approximately one-fifth, (19.2%) of participants cared for more than 15 ostomy patients monthly. The remaining 34% cared for 6-15 patients monthly. Mean number of ostomy patients seen was 25, with a range of one to three hundred. Participants reported caring for the following type of ostomy patients; 98.3% had experience caring for patients with a colostomy, 88.2% cared for patients with an ileostomy and 81.9% cared for patients with a urostomy.

Study Scoring

For the 297 study participants, the mean overall percentage of correct answers was 82.23%. Table two reports the breakdown of overall scores by scenario and by self reported level of ostomy care knowledge. The 229 participants who were recruited from the vendor's list had a mean overall correct percentage of 82.01% and the 68 participants who were recruited from the list provided by the study sponsor had a mean overall correct percentage of 91.71%. This was not unexpected due to expertise in ostomy care and product familiarity of those currently within the study sponsor's database. See Example 2 (Exemplary Scenario Answer Key).

Implications for Education, Clinical Practice and Research

The Ostomy Algorithm has substantial implications for health education. It can act as a helpful assistive device for the training and re-training of non-expert clinicians and offers a great review of critical care components and assessment parameters for ostomy care for WOC experts. Potentially it can be used for patient education as well as staff development. The algorithm could also be a source of competency documentation if linked with training modules and testing procedures. The algorithm has the potential to influence international quality of care and may be a source to support legally defensible ostomy care and staff development. If translated into other languages, the algorithm has the potential to improve ostomy care education and delivery across the world.

The Ostomy Algorithm has the potential to profoundly affect the quality of patient care. Because of its digital format and because its components are based on research evidence and expert insights, the algorithm offers point of care access at the bedside for evidence-based care delivery enhancing patient safety. The digital "24-7" assistance may promote safer more cost effective care until the patient can be seen by a specialist. The algorithm may help staff have more confidence in their ostomy care knowledge and interventions. Another benefit of algorithm use may be in the form of "cognitive residue." Staff clinicians may find they become faster and safer in care situations as the algorithm steps become more embedded in providers' cognitive processes.

Example 2—Exemplary Answer Key for Algorithm Validation Study

For each practice scenario in the validation study of Example 1, participant answers were scored against an answer key such as that provided in Tables 11-21. Each key provides best, acceptable, and incorrect answers for both the involved ostomy assessment and correlated ostomy management options.

TABLE 11

| PRACTICE SCENARIO | BEST ANSWER | ACCEPTABLE ANSWER(S) | INCORRECT ANSWER(S) |
|---|---|---|---|
| 1a. Type of ostomy | Ileostomy | None | Colostomy Urostomy |
| 1b. Management options | Drainable Pouch (Option 1) | Closed-end pouch (patient personal preference only) Urostomy pouch (only if output totally liquid) (Options 2, 3) | None |

TABLE 12

| PRACTICE SCENARIO | BEST ANSWER | ACCEPTABLE ANSWER(S) | INCORRECT ANSWER(S) |
|---|---|---|---|
| 2a. Type and Volume of Output | Liquid | None | Pasty-soft stool Oatmeal consistency Similar to that of intact colon Urine |
| 2b. Management options | Extended wear skin barriers (Durahesive ®) (Option 5) | Regular wear skin barriers (Stomahesive ®) High Volume Output pouch (SUR-FIT Natura ®) (Options 4, 6) | None |

TABLE 13

| PRACTICE SCENARIO | BEST ANSWER | ACCEPTABLE ANSWER(S) | INCORRECT ANSWER(S) |
|---|---|---|---|
| 3a. Stoma type | End Stoma | | Double Barrel Stoma Loop Stoma |
| 3b. Management Options | Not Applicable | None | Special considerations for Loop Device & Double Barrel Stoma (Options 7, 8) |

TABLE 14

| PRACTICE SCENARIO | BEST ANSWER | ACCEPTABLE ANSWER(S) | INCORRECT ANSWER(S) |
| --- | --- | --- | --- |
| 4a. Stoma Profile | Ideal Stoma | None | Flush Stoma<br>Long Stoma |
| 4b. Management Options | Two-piece pouching system (Natura ®, Esteem synergy ®) (Option 10) | One-piece pouch (ActiveLife ®, Esteem ®) (Option 9) | Convex pouching system (Natura ®, ActiveLife ®, Esteem ®, Esteem synergy ®) (Option 11) |

TABLE 15

| PRACTICE SCENARIO | BEST ANSWER | ACCEPTABLE ANSWER(S) | INCORRECT ANSWER(S) |
| --- | --- | --- | --- |
| 5a. Stoma Shape | Round | None | Oval<br>Irregularly Shaped<br>Mushroom Shaped |
| 5b. Management Options | Moldable skin barriers (Option 12) | Cut-to-fit skin barriers (Option 13) | Pre-cut skin barriers (Option 14) |

TABLE 16

| PRACTICE SCENARIO | BEST ANSWER | ACCEPTABLE ANSWER(S) | INCORRECT ANSWER(S) |
| --- | --- | --- | --- |
| 6a. Abdominal Contour | Round & Protruding | None | Soft & Flaccid<br>Firm & Flat |
| 6b. Management Options | Two-piece pouching system (Natura ®, Esteem synergy ®) (Option 10) | One-piece pouch (ActiveLife ®, Esteem ®) (Option 9) | Convex pouching system (Natura ®, ActiveLife ®, Esteem ®, Esteem synergy ®) (Option 11) |

TABLE 17

| PRACTICE SCENARIO | BEST ANSWER | ACCEPTABLE ANSWER(S) | INCORRECT ANSWER(S) |
| --- | --- | --- | --- |
| 7a. Level Pouching Surface | Pouching Surface near incision | Level Pouching Surface | Stoma in skin fold |
| 7b. Management Options | Protect Incision from contamination by stool<br>No Accessory Products Required (Option 19) | Skin barrier paste (Stomahesive ®)<br>Skin barrier seals (Eakin ® seals)<br>Skin barrier strips (Stomahesive ® strips) (Options 15, 16, 17, 18) | None |

TABLE 18

| PRACTICE SCENARIO | BEST ANSWER | ACCEPTABLE ANSWER(S) | INCORRECT ANSWER(S) |
| --- | --- | --- | --- |
| 8a. Presence/ Absence of Devices | No Device Present | None | Loop Rods/Stoma Bridges<br>Ureteral Stents<br>Special considerations for loop ostomies<br>Exercise caution so as not to dislodge ureteral stents (Options 20, 21) |
| 8b. Management Options | None | None | |

TABLE 19

| PRACTICE SCENARIO | BEST ANSWER | ACCEPTABLE ANSWER(S) | INCORRECT ANSWER(S) |
| --- | --- | --- | --- |
| 9a. Presence/ Absence of Stoma Complications | No stoma complication present | None | Parastomal Hernia<br>Stomal prolapse<br>Retracted stoma<br>Stoma Stenosis<br>Stoma Necrosis<br>Mucocutaneous Separation |
| 9b. Management Options | None | None | Any that are chosen (Options 22, 23, 24, 25, 26, 27, 28, 29, 30, 31, 32, 33, 34, 35, 36, 37) |

TABLE 20

| PRACTICE SCENARIO | BEST ANSWER | ACCEPTABLE ANSWER(S) | INCORRECT ANSWER(S) |
|---|---|---|---|
| 10a. Peristomal Skin Assessment (Lesion (L) Classification) | No Lesion Present | No Lesion Present | Any responses would render this answer incorrect |
| 10B. Peristomal Skin Assessment (Location (T) Classification) | No Lesion Present | No Lesion Present | Any responses would render this answer incorrect |

TABLE 21

| PRACTICE SCENARIO | BEST ANSWER | ACCEPTABLE ANSWER(S) | INCORRECT ANSWER(S) |
|---|---|---|---|
| 11a. Presence/Absence of Peristomal Skin Complications | No peristomal skin complication present | No peristomal skin complication present | Candidiasis Folliculitis Irritant Contact Dermatitis Allergic Contact Dermatitis Pseudoverrucous Lesion Peristomal Pressure Ulcer Pyoderma Gangrenosum |
| 11b. Management Options | None | None | Any that are chosen (Options 38, 39, 40, 41, 42, 43, 44, 45, 46, 47, 48, 49, 50, 51, 52) |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES

1. Bales I. Testing a computer-based ostomy care training resource for staff nurses. *Ostomy Wound Management.* 2010; 56(5):60-69.
2. Beitz J, Gerlach M A, Ginsburg P, Ho M, McCann E, Schafer V, et al. Content validation of a standardized algorithm for ostomy care. *Ostomy Wound Management.* 2010; 56(10):22-38.
3. Boarini J, Colwell J, McNichol L L, Carmel J E, Goldberg M T, Pruitt L D. Roles of the ostomy nurse specialist: historical perspective, role potential. In: Colwell J, Goldberg M T, Carmel J E. Fecal and Urinary Diversions Management Principles. St. Louis: Mosby; 2004. 22.
4. Jones T, Springfield T, Brudwick M, Ladd A. Fecal ostomies practical management for the home health clinician. *Home Healthcare Nurse.* 2011; 29(5):306-317.
5. Wound Ostomy and Continence Nursing Society. Management of the patient with a fecal ostomy: Best practice guideline for clinicians. Mount Laurel, N.J. 2010.
6. Cross H. Staff nurses confidence and barriers in caring for ostomy patients. *Journal of Wound Ostomy and Continence Nursing.* 2012; 39(3) (suppl). Abstract 6002.
7. Turnbull G B. The importance of coordinating ostomy care and teaching across settings. *Ostomy Wound Management.* 2002; 48(5); 12-13.
8. Wound, Ostomy and Continence Nursing Society. 2008 WOC nursing productivity and salary survey. Mount Laurel, N J.
9. Wound, Ostomy and Continence Nursing Society. 2012 WOC nursing productivity and salary survey. Mount Laurel, N J.
10. Agency for Healthcare Research and Quality. Patient Safety and Quality: An Evidence-Based Handbook for Nurses: Publication No. 08-0043. Rockville, Md.: Agency for Healthcare Research and Quality; April 2008.

What is claimed is:

1. A method of administering an ostomy care device or product to an individual in need thereof, the method comprising:
   a) assessing any stoma devices present in or on a stoma of the individual, wherein assessing any stoma devices present comprises selecting a stoma device determined to be present in or on a stoma of the individual from a list of potential stoma devices, the list of potential stoma devices comprising: rod or bridge, stent, and the absence of rod, bridge, and stent in or on a stoma of the individual, and assessing one or more components of the individual selected from: skin adjacent an ostomy, topographical location of any peristomal lesion, stoma type, pouching surface, and stoma complications to generate ostomy care device or product assessment information; wherein each component assessment comprises selecting any conditions for the component determined to be present for the individual from a list of potential conditions for the component;
   b) applying an algorithm to the ostomy care device or product assessment information, the algorithm executable by a computer in response to input, by a non-expert or non-specialized ostomy care clinician, associating the assessment information with text descriptions or images selected from a set of text descriptions and images, and selecting, from the list of potential conditions, any conditions present for the component determined to be present for the individual, the algorithm providing one or more recommendations comprising ostomy care device or product recommendations based on pre-established criteria, at least one recommended ostomy care device or product having features corresponding to the assessment information including the assessment of any stoma device determined to be present and the assessment of the one or more components of the individual; and c) administering the at least one ostomy care device or product based on the one or more ostomy care device or product recommendations;

wherein the method is capable of being performed by at least the non-expert or non-specialized ostomy care clinician.

2. The method of claim 1, wherein the algorithm provides the one or more ostomy care device or product recommendations by matching the ostomy care device or product assessment information to at least one ostomy care product or device.

3. The method of claim 1, wherein assessing the component of skin adjacent an ostomy comprises selecting any skin conditions determined to be present for the individual from a list of potential skin conditions, the list of potential skin conditions comprising: healthy skin, hyperemic lesion, erosive lesion, ulcerative lesion, ulcerative lesion with non-viable tissue, and proliferative lesion.

4. The method of claim 1, wherein assessing the component of topographical location of any peristomal lesion comprises selecting any peristomal lesion locations determined to be present for the individual from a list of potential peristomal lesion locations, the list of potential peristomal lesion locations comprising: upper right quadrant, lower right quadrant, lower left quadrant, upper left quadrant, and all quadrants.

5. The method of claim 1, wherein assessing the component of stoma type comprises selecting any stoma type determined to be present for the individual from a list of potential stoma types, the list of potential stoma types comprising: flush, narrow oval, and the absence of flush and narrow oval stoma types present for the individual.

6. The method of claim 1, wherein assessing the component of pouching surface comprises selecting any pouching surface determined to be present for the individual from a list of potential pouching surfaces, the list of potential pouching surfaces comprising: soft and flaccid abdomen, stoma in a crease or a skin fold, pouching area near incision, and the absence of soft and flaccid abdomen, stoma in a crease or a skin fold, and pouching area near incision present for the individual.

7. The method of claim 1, wherein assessing the component of stoma complications comprises selecting any stoma complications determined to be present for the individual from a list of potential stoma complications, the list of potential stoma complications comprising: retracted stoma, hernia, prolapsed stoma, mucotaneous separation, dark stoma color, and the absence of retracted stoma, hernia, prolapsed stoma, mucotaneous separation, and dark stoma color present for the individual.

8. A method of administering an ostomy care device or product to an individual in need thereof, the method comprising:

a) assessing any stoma devices present in or on a stoma of the individual, wherein assessing any stoma devices present comprises selecting a stoma device determined to be present in or on a stoma of the individual from a list of potential stoma devices, the list of potential stoma devices comprising: rod or bridge, stent, and the absence of rod, bridge, and stent in or on a stoma of the individual; and assessing one or more components of the individual selected from: skin adjacent an ostomy, topographical location of any peristomal lesion, stoma type, pouching surface, and stoma complications; wherein each component assessment comprises selecting any conditions for the component determined to be present for the individual from a list of potential conditions for the component;

b) applying an algorithm to the assessment, the algorithm executable by a computer in response to input, by a non-expert or non-specialized ostomy care clinician, associating the assessment information with text descriptions and images selected from a set of text descriptions and images, and selecting, from the list of potential conditions, any conditions determined to be present for the individual, the algorithm providing at least one ostomy care device or product recommendation based on pre-established criteria, at least one recommended ostomy care device or product having features corresponding to the assessment information including the assessment of any stoma device determined to be present and the assessment of the one or more components of the individual; and c) administering the at least one ostomy care device or product to the individual based on the at least one ostomy care device or product recommendation;

wherein the method is capable of being performed by at least the non-expert or non-specialized ostomy care clinician.

9. A method of administering ostomy care guidance to an individual in need thereof, the method comprising:

a) assessing one or more determined components of: stoma devices present in or on a stoma of the individual, skin adjacent an ostomy, topographical location of any peristomal lesion, stoma type, pouching surface, and stoma complications to generate ostomy care device or product assessment information, wherein each component assessment comprises selecting any conditions for the component determined to be present for the individual from a list of potential conditions for the component;

b) applying an algorithm to the ostomy care assessment information, the algorithm executable by a computer in response to input, by a non-expert or non-specialized ostomy care clinician, associating the assessment information with text descriptions and images from a set of text descriptions and images, and selecting, from the list of potential conditions, any conditions present for the component determined to be present for the individual, the algorithm providing one or more ostomy care device or product recommendations based on pre-established criteria, at least one recommended ostomy care device or product having features corresponding to the assessment information including the assessment of any stoma device determined to be present and the assessment of the one or more components of the individual; and c) administering the at least one recommended ostomy care device or product to the individual;

wherein the method is capable of being performed by at least the non-expert or non-specialized ostomy care clinician.

10. The method of claim 1, wherein the determined stoma device is an observed stoma device and the determined components are observed components.

11. The method of claim 8, wherein the determined stoma device is an observed stoma device and the determined components are observed components.

12. The method of claim 1, wherein the stoma devices present in or on a stoma of the individual further comprises a barrier around the stoma of the individual.

13. The method of claim 8, wherein the stoma devices present in or on a stoma of the individual further comprises a barrier around the stoma of the individual.

14. The method of claim 9, wherein the stoma devices present in or on a stoma of the individual further comprises a barrier around the stoma of the individual.

* * * * *